(12) United States Patent
Kodali et al.

(10) Patent No.: US 9,315,650 B2
(45) Date of Patent: Apr. 19, 2016

(54) BIO-RENEWABLE PLASTICIZERS DERIVED FROM VEGETABLE OIL

(71) Applicant: Regents of the University of Minnesota, Saint Paul, MN (US)

(72) Inventors: Dharma R. Kodali, Plymouth, MN (US); Lucas J. Stolp, Minneapolis, MN (US); Mrinal Bhattacharya, Woodbury, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 434 days.

(21) Appl. No.: 13/771,803

(22) Filed: Feb. 20, 2013

(65) Prior Publication Data

US 2013/0228097 A1 Sep. 5, 2013

Related U.S. Application Data

(63) Continuation-in-part of application No. PCT/US2011/050200, filed on Sep. 1, 2011.

(60) Provisional application No. 61/382,184, filed on Sep. 13, 2010.

(51) Int. Cl.

| | |
|---|---|
| *C07C 67/08* | (2006.01) |
| *C07C 69/67* | (2006.01) |
| *C07C 67/26* | (2006.01) |
| *C07C 69/675* | (2006.01) |
| *C08K 5/10* | (2006.01) |
| *C08K 5/101* | (2006.01) |
| *C11C 3/00* | (2006.01) |
| *C11C 3/08* | (2006.01) |
| *C08L 27/06* | (2006.01) |

(52) U.S. Cl.
CPC . *C08K 5/10* (2013.01); *C07C 67/08* (2013.01); *C07C 67/26* (2013.01); *C07C 69/67* (2013.01); *C07C 69/675* (2013.01); *C08K 5/101* (2013.01); *C08L 27/06* (2013.01); *C11C 3/00* (2013.01); *C11C 3/003* (2013.01); *C11C 3/006* (2013.01); *C11C 3/08* (2013.01)

(58) Field of Classification Search
CPC ........ C07C 67/08; C07C 69/67; C07C 67/26; C07C 69/675; C08K 5/10; C08K 5/101; C11C 3/00; C11C 3/003; C11C 3/006; C11C 3/08; C08L 27/06
USPC ........................................................ 524/313
See application file for complete search history.

(56) References Cited

U.S. PATENT DOCUMENTS

| | | |
|---|---|---|
| 5,075,046 A | 12/1991 | Stoll |
| 6,018,063 A | 1/2000 | Isbell et al. |
| 6,734,241 B1 | 5/2004 | Nielsen et al. |
| 6,797,753 B2 | 9/2004 | Benecke et al. |
| 6,949,597 B2 | 9/2005 | Nielsen et al. |
| 7,196,124 B2 | 3/2007 | Parker et al. |

FOREIGN PATENT DOCUMENTS

| | | |
|---|---|---|
| DE | 4433958 A1 | 3/1996 |
| WO | WO2009033240 A1 | 3/2009 |
| WO | WO2009138508 A1 | 11/2009 |

OTHER PUBLICATIONS

International Preliminary Report on Patentability; Mar. 28, 2013; World Intellectual Property Organization (WIPO) (International Bureau of); PCT/US2011/050200; 6 pages.
International Search Report and Written Opinion; Apr. 25, 2012; World Intellectual Property Organization (WIPO) (International Bureau of); PCT/US2011/050200; 9 pages.

*Primary Examiner* — Angela C Scott
(74) *Attorney, Agent, or Firm* — Fish & Richardson P.C.

(57) ABSTRACT

A composition includes estolide esters of vegetable oil fatty acid alkyl esters where the vegetable oil has an unsaturation greater than 90 IV. The fatty acid alkyl esters include unsaturated and saturated fatty acid alkyl esters, and each unsaturated fatty acid alkyl ester has greater than one estolide ester functionality.

20 Claims, 20 Drawing Sheets

BIO-RENEWABLE PLASTICIZERS DERIVED FROM VEGETABLE OIL

CROSS-REFERENCE TO RELATED APPLICATIONS

This application is a continuation-in-part of, and claims benefit under 35 U.S.C. §120 to PCT/US2011/050200, with an international filing date of Sep. 1, 2011, which claims priority to under 35 U.S.C. §119e to U.S. Provisional Application Ser. No. 61/382,184, filed on Sep. 13, 2010, the entire content of which is hereby incorporated by reference.

TECHNICAL FIELD

This invention relates to vegetable oil-derived compounds useful as plasticizers.

BACKGROUND

Plasticizers are non-volatile liquid compounds that impart flexibility to polymers and increase their range of end applications. The majority of plasticizers are used in the utilization of polyvinylchloride (PVC). PVC, due to its unique combination of price, performance, and versatile use, is one of the oldest and widely used high volume plastics. The PVC products formulated with various additives, range from very rigid pipes and siding to flexible flooring, sheeting, and adhesives. The compounding of PVC includes multifunctional additives that modify the properties; in general the formulations contain the polymer (resin), thermal stabilizers, fillers, plasticizers, and other specific property enhancers such as fire resistant materials. Rigid PVC may contain low levels of plasticizer usually less than 20 phr (parts per hundred parts resin) and is primarily used for pipe work, ducts, and similar applications where structural rigidity and chemical resistance is required. Flexible PVC contains high concentrations of plasticizer (up to 100+ phr) and is useful for numerous applications such as films, sheeting, cable coverings, moldings, stationary products, toys, hoses, leather goods, clothing and various furnishings.

The dominant class of plasticizers used in the vinyl industry today is the petroleum-derived phthalates. These compounds are produced by reacting phthalic anhydride with two equivalents of alcohol to form a diester. The largest produced phthalate for the vinyl industry is dioctyl phthalate (DOP).

Materials derived from natural/renewable resources have been proposed as alternatives to phthalate plasticizers. One example is a fully acylated monoglyceride ester derived from hydrogenated caster oil described, e.g., in U.S. Pat. No. 6,734,241 and U.S. Pat. No. 6,949,597, and sold under the name "Soft-n-Safe" by Danisco. Other examples include epoxidized fatty acid esters derived from epoxidized oils, such as linseed and soybean, trans-esterified with various polyols, as described, e.g., in U.S. Pat. No. 6,797,753. Yet another example, described in WO2009/033240, features a mixture of glycerol esters containing natural fatty acyl chains and short acetyl groups, along with fatty acid ethyl esters. It appears that the unsaturated fatty acids are not modified and there are no fatty acyl chain backbone modifications to increase the polarity.

SUMMARY

A composition is described that includes estolide esters of vegetable oil fatty acid alkyl esters where the vegetable oil has an unsaturation of greater than 90 Iodine Value ("IV"). Examples include soybean oil, canola oil, rapeseed oil, sunflower oil, corn oil, safflower oil, camelina oil, and linseed oil.

An "estolide ester" is an aliphatic ester esterified to the backbone carbons of a long chain unsaturated fatty acid at the site of unsaturation. Vegetable oils contain both saturated and unsaturated fatty acids. The estolide esters are acyl chains attached to the backbone carbons of the fatty acid at the site of unsaturation (e.g., linoleic acid, α-linoleic acid, and oleic acid). Each unsaturated fatty acid alkyl ester has greater than one estolide ester functionality.

The vegetable oil fatty acid alkyl esters can be $C_1$-$C_4$ alkyl esters. Examples include methyl and isobutyl esters. In some embodiments, both methyl and isobutyl esters are present. In some embodiments, the unsaturated fatty acid alkyl esters are fully estolided. By "fully estolided," it is meant that all available unsaturated reaction sites are reacted to form an estolide ester functionality. Examples of suitable estolide esters include esters derived from carboxylic acids having 1 to 4 carbon atoms, e.g., acetate esters.

The estolide esters may be prepared according to a process that includes: (a) treating the vegetable oil fatty acid alkyl esters with an oxidizing agent to form a reaction product comprising epoxy and hydroxyl groups covalently bonded to the fatty acid alkyl esters at the site of unsaturation; and (b) treating the reaction product with an acylating agent to react the epoxy and hydroxyl groups to form estolide esters covalently bonded to the unsaturated fatty acid alkyl esters such that each fatty acid alkyl ester has on average greater than one estolide ester functionality. The reaction with the acylating agent to form the estolide esters occurs in the absence of a catalyst.

In some embodiments, the process includes: (a) treating the vegetable oil fatty acid alkyl esters with a lower carboxylic acid and an oxidizing agent comprising hydrogen peroxide to form the reaction product comprising epoxy and hydroxyl groups covalently bonded to the fatty acid alkyl esters at the site of unsaturation; and (b) treating the reaction product with the acylating agent to form the estolide esters. Step (b) occurs in the absence of a catalyst.

In some embodiments, the process includes: (a) treating the vegetable oil fatty acid alkyl esters with a peroxy lower carboxylic acid to form a first reaction product comprising epoxy fatty acid alkyl esters; (b) treating the first reaction product with a lower carboxylic acid to form a second reaction product comprising hydroxyl-acetoxy fatty acid alkyl esters; and (c) treating the second reaction product with the acylating agent to form the estolide esters. Step (c) occurs in the absence of a catalyst.

In still other embodiments, the process includes treating the first reaction product with the lower carboxylic acid together with the acylating agent to form the estolide esters.

The compositions are useful as plasticizing agents when combined with a polymer such as polyvinyl chloride, or biopolymers such as polylactides or cellulosics (e.g., cellulose acetate), in an amount sufficient to plasticize the polymer or biopolymer.

The details of one or more embodiments of the invention are set forth in the description below. Other features, objects, and advantages of the invention will be apparent from the description and from the claims.

DETAILED DESCRIPTION

Compositions that include estolided esters of vegetable oil fatty acid alkyl esters, where the vegetable oil has an unsaturation greater than 90 IV, as well as a method of making the compositions, are described in the Summary of the Invention, above. The invention will now be described further by way of the following examples.

EXAMPLES

Materials

Glacial acetic acid was purchased from Alfa Aesar (Ward Hill, Mass.). Soybean oil and Soy Fatty Acid Methyl Ester (SFAME) or soy biodiesel was obtained from Cargill Inc. (Minneapolis, Minn.). Hydrogen peroxide (50% w/w $H_2O$), anhydrous 2-methyl-1-propanol or isobutanol (99.5%), sodium methoxide (reagent grade), and acetic anhydride (99.5%) were purchased from Sigma-Aldrich Chemical Co. (Milwaukee, Wis.). Stabilized PVC with thermal stabilizers and lubricants, Formula D (see Table 1) was obtained from Aspen Research Corporation (Whitebear Lake, Minn.). Hexanes (technical grade-for extractions), diethyl ether (laboratory grade), diisopropyl ether (certified), and sulfuric acid (ACS+) were purchased from Fischer Scientific (Pittsburgh, Pa.). Sodium chloride (ACS) and sodium sulfate (ACS) were purchased from Mallinckrodt Chemical (Hazelwood, Mo.). Sodium acetate was purchased from Matheson Coleman & Bell (Gardena, Calif.). Sodium bicarbonate (reagent) was purchased from J. T. Baker (Phillipsburg, N.J.). Magnesol® R60 was obtained from The Dallas Group of America Inc. (Whitehouse, N.J.). TLC was preformed on Analtech (Newark, Del.) Unisil GF 250 μm silica plates, charred on a hot plate after spraying with 50% sulfuric acid.

TABLE 1

Formula D Composition.

| Type | Weight Fraction | Phr |
|---|---|---|
| Resin (Oxyvinyl 216) | 0.95238 | 100.0 |
| Calcium Stearate | 0.01429 | 1.5 |
| Amide Wax | 0.02381 | 2.5 |
| Mercapto-Tin | 0.00952 | 1.0 |

Instrumentation and Methods

$^1$H NMR spectra were recorded on a Varian Unity 200 (Palo Alto, Calif.) 200 MHz spectrophotometer with a 4-nucleous probe and auto sampler. All experiments were run using $CDCl_3$ as a solvent. The integration of the proton chemical shifts to determine the number of protons for methyl and isobutyl esters listed in Tables 2-3 and 5-7 were based on the terminal methyl peak at 0.88 ppm. The integration of the proton chemical shifts to determine the number of protons for the isobutyl/methyl (70/30) esters was based on the α-methylene peak at 2.25 ppm.

IR spectra were obtained on a MIDAC Corp. (Costa Mesa, Calif.) M-Series FTIR neat using NaCl disks. The regions of each spectrum monitored were: C=O stretches of acids (1705-1720) and esters (1735-1750), =C—H stretches of alkenes (3000-3100), and the O—H stretches of acids (2500-3300) and hydroxyls (3200-3550).

Figure 4:
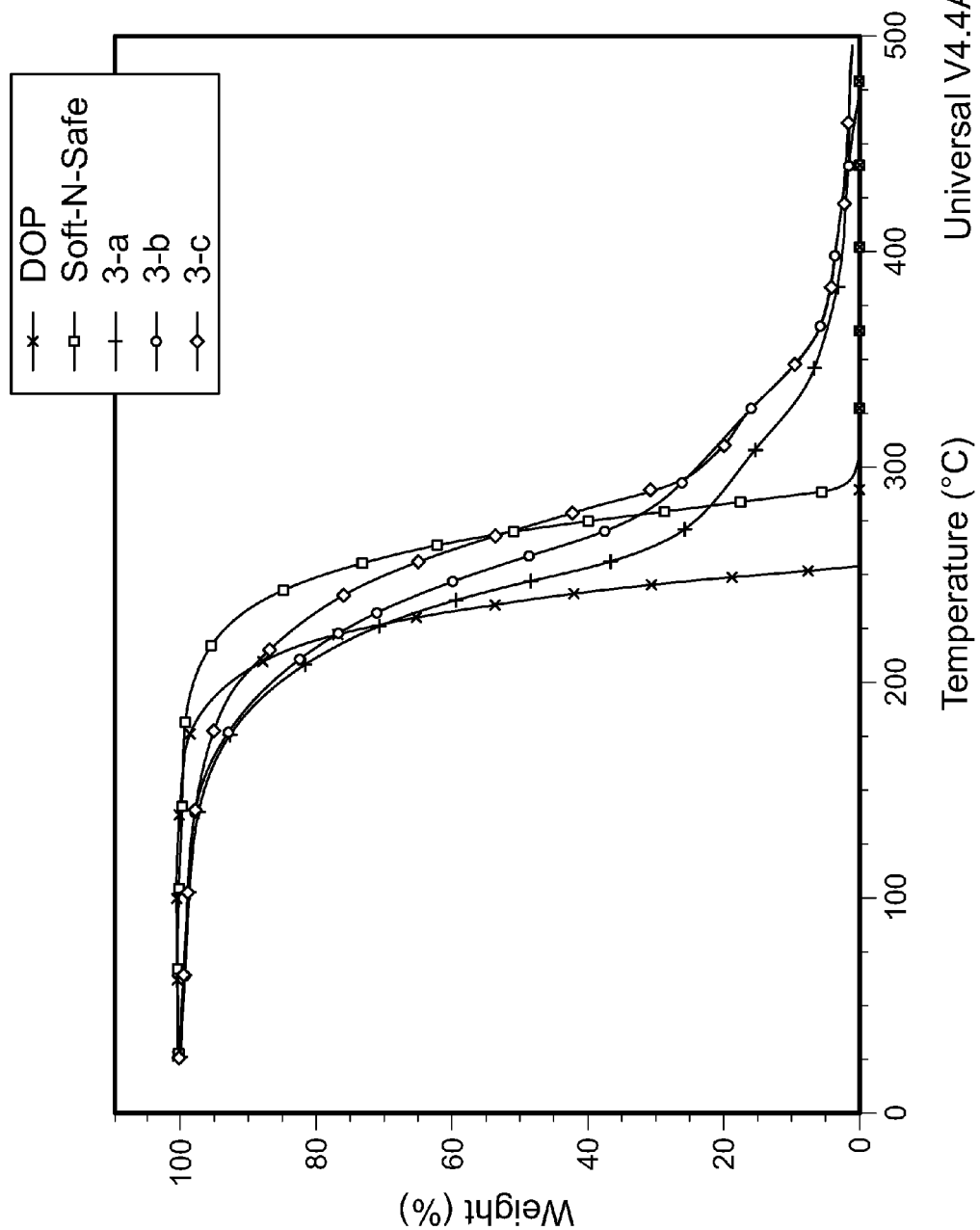
FIG. 4 depicts thermogravimetric analysis of plasticizers according to the invention (3-a to 3-c), and commercial plasticizers DOP and SnS.
Figure 5:
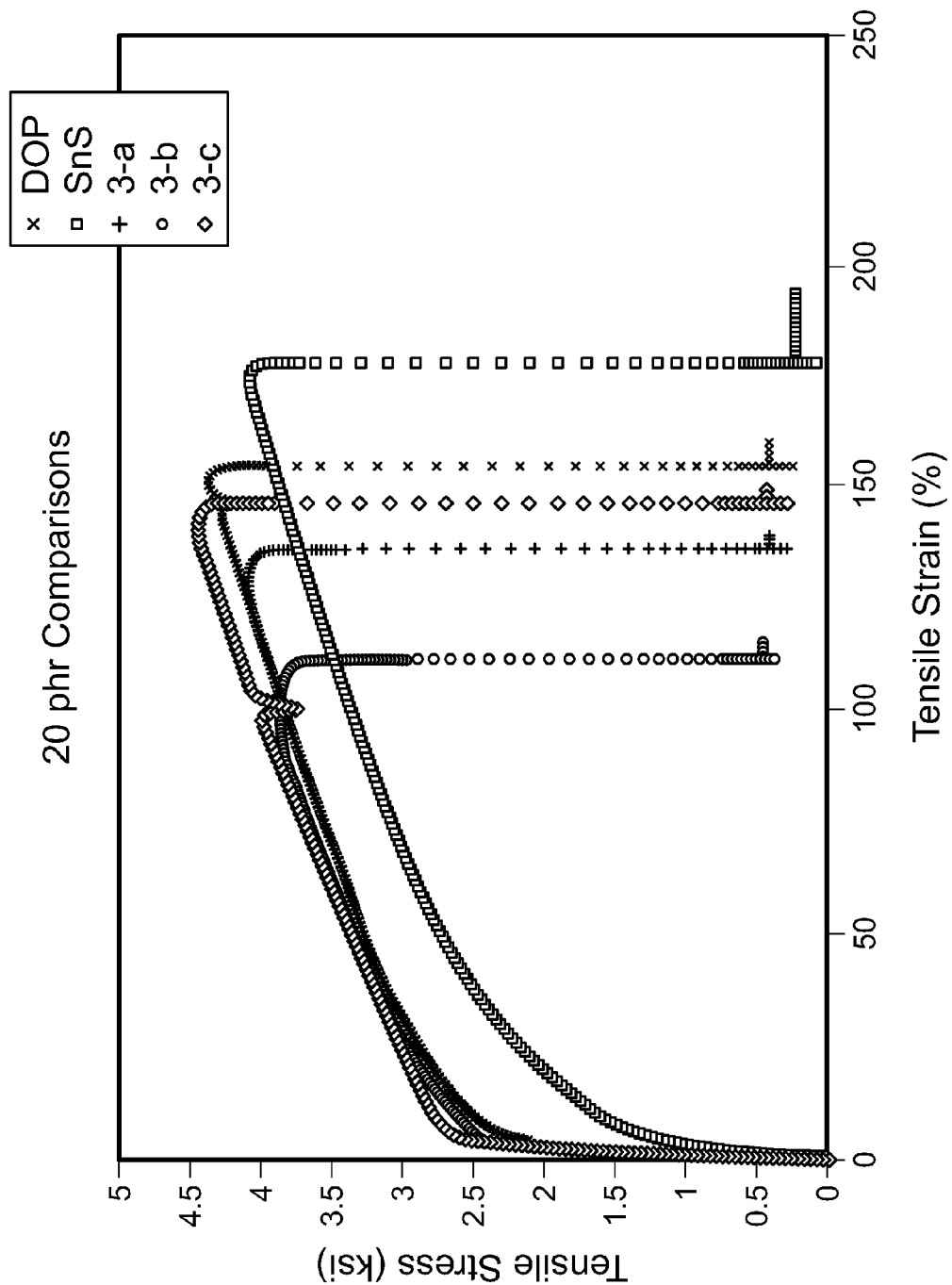
FIG. 5 depicts stress-strain curves for PVC samples compounded with plasticizers according to the invention (3-a to 3-c), and commercial plasticizers DOP and SnS, at a 20 phr plasticizer loading.
Figure 6:
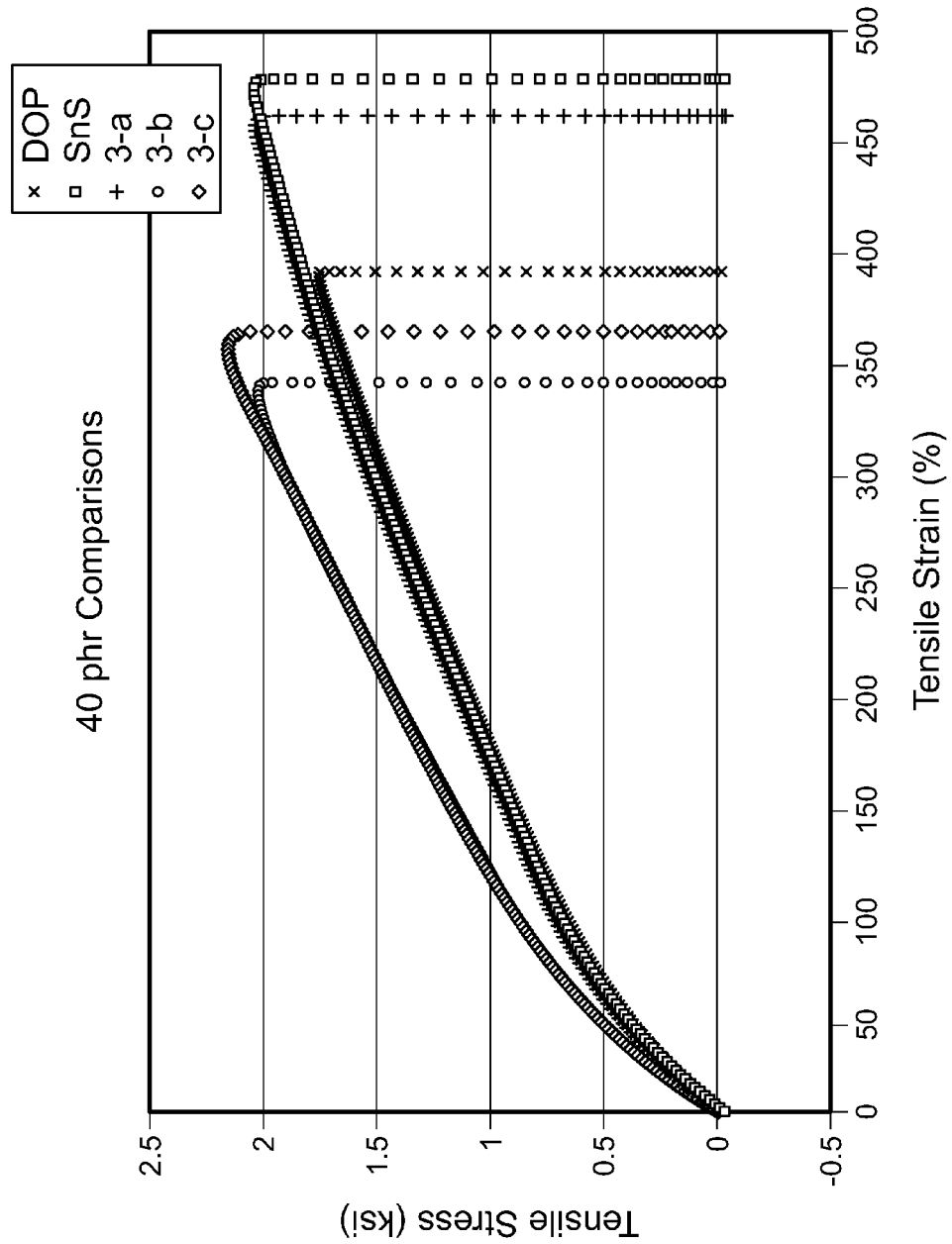
FIG. 6 depicts stress-strain curves for PVC samples compounded with plasticizers according to the invention (3-a to 3-c), and commercial plasticizers DOP and SnS, at a 40 phr plasticizer loading.
Figure 7:
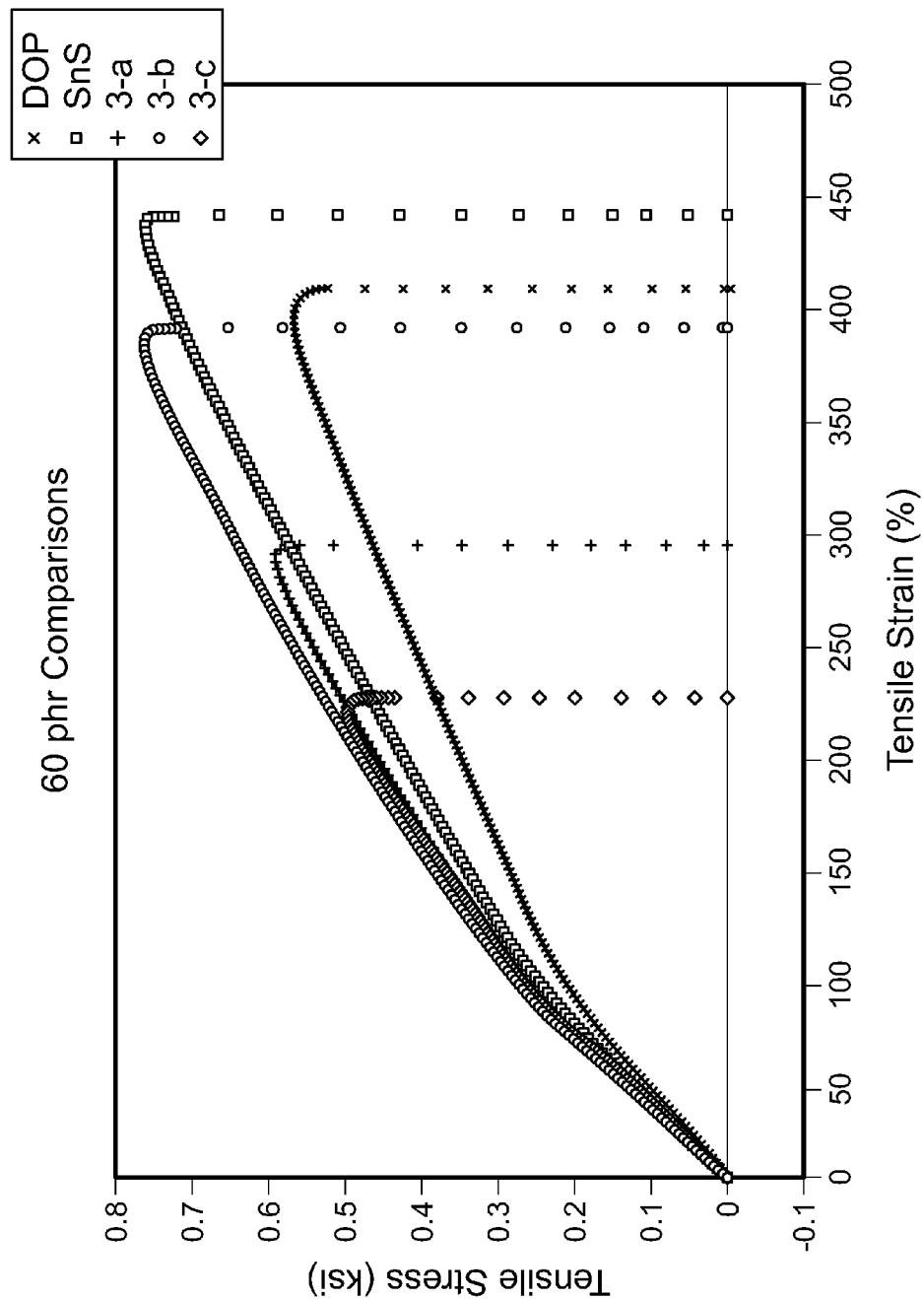
FIG. 7 depicts stress-strain curves for PVC samples compounded with plasticizers according to the invention (3-a to 3-c), and commercial plasticizers DOP and SnS, at a 60 phr plasticizer loading.
Figure 8:
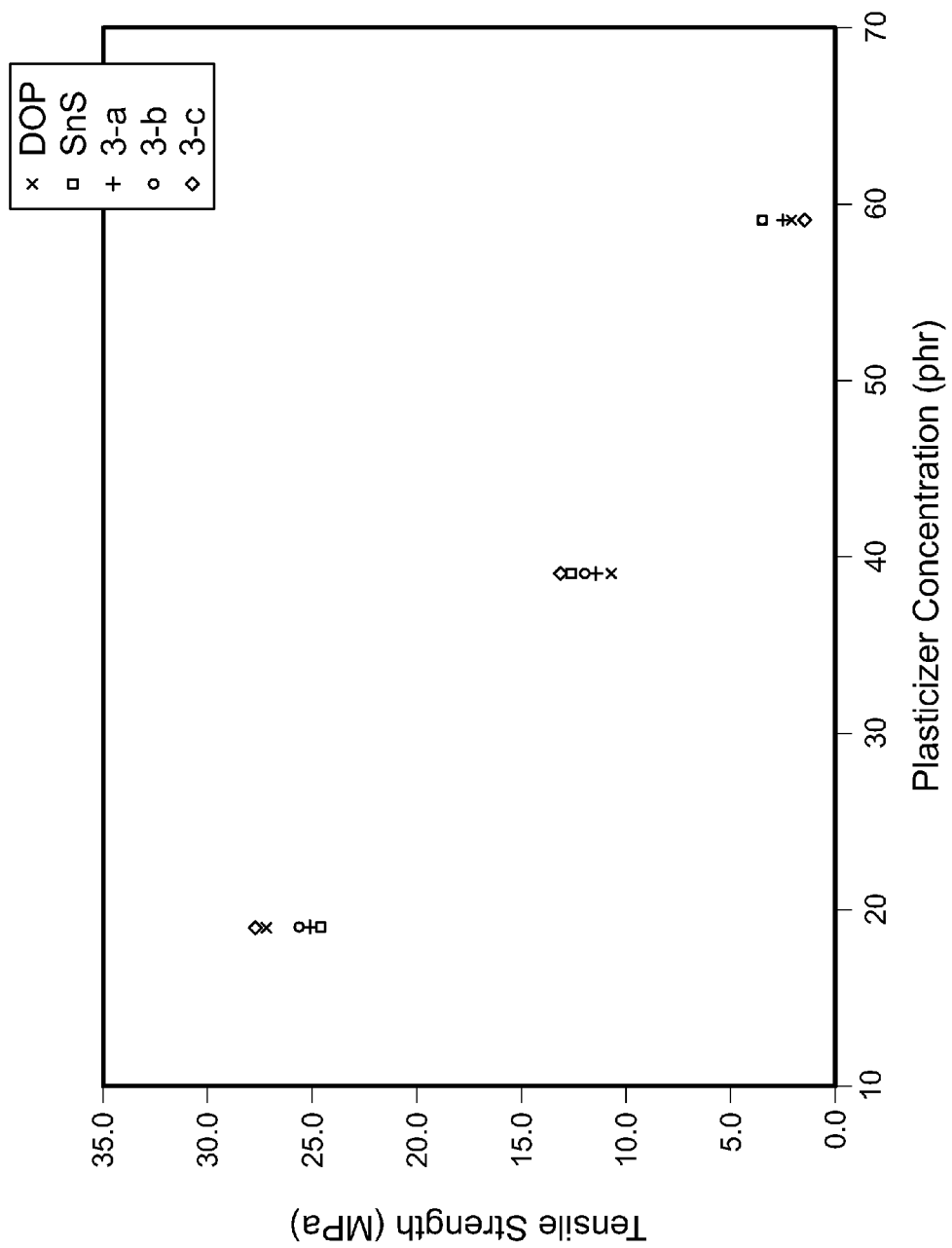
FIG. 8 depicts tensile strength at break for PVC samples compounded with plasticizers according to the invention (3-a to 3-c), and commercial plasticizers DOP and SnS, at various plasticizer loadings.
Figure 9:
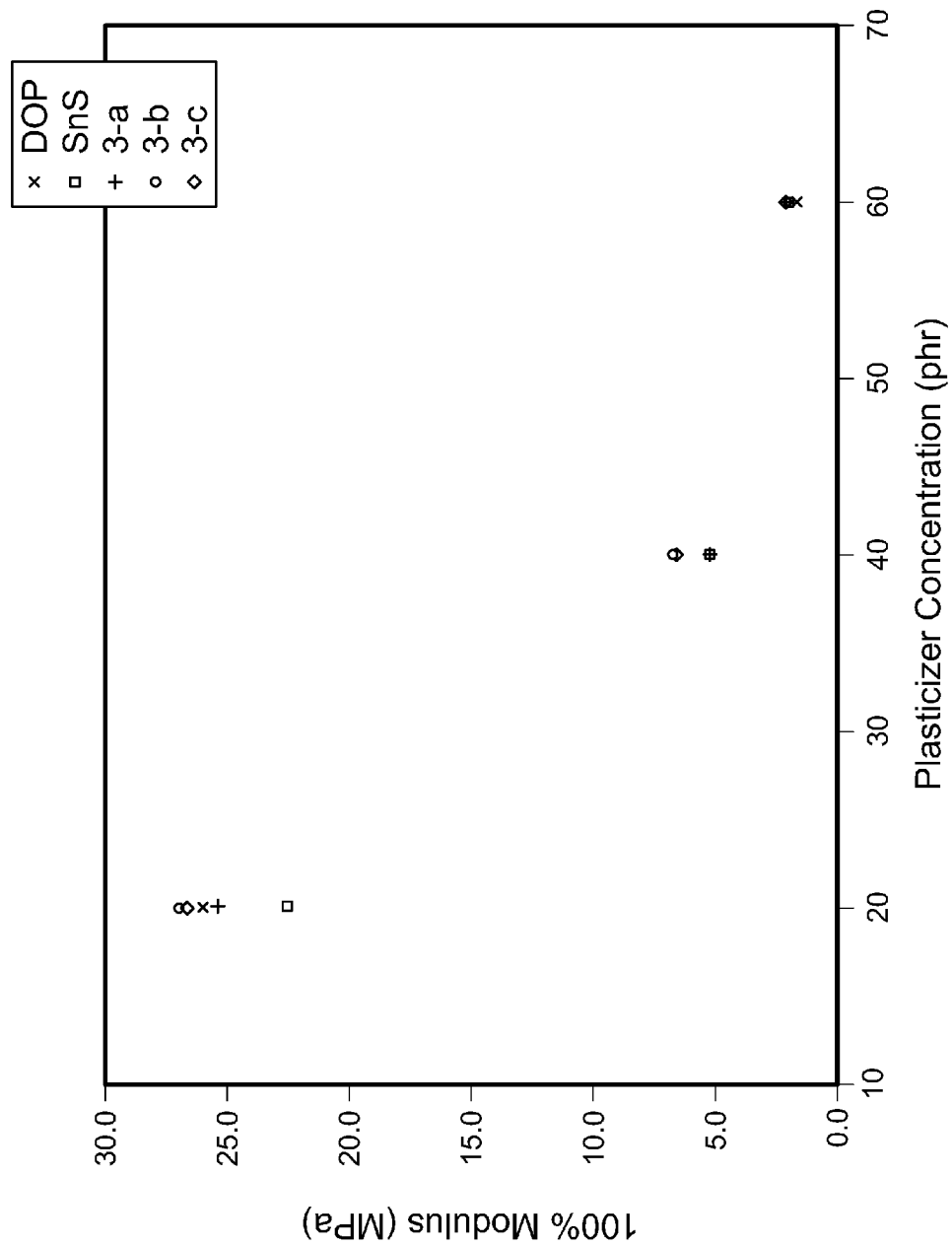
FIG. 9 depicts 100% modulus for PVC samples compounded with plasticizers according to the invention (3-a to 3-c), and commercial plasticizers DOP and SnS, at various plasticizer loadings.
Figure 10:
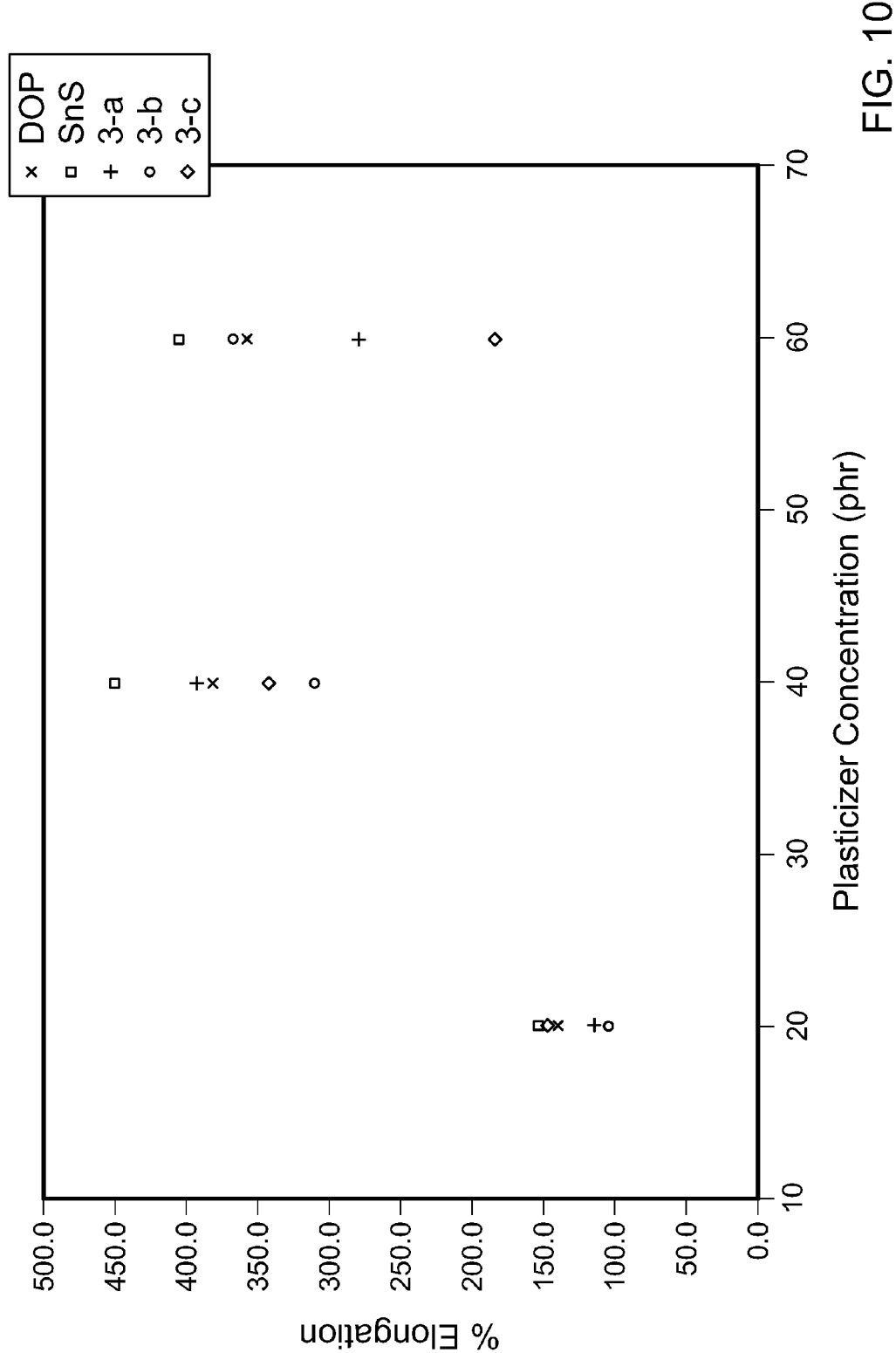
FIG. 10 depicts percent elongation for PVC samples compounded with plasticizers according to the invention (3-a to 3-c), and commercial plasticizers DOP and SnS, at various plasticizer loadings.
Figure 11:
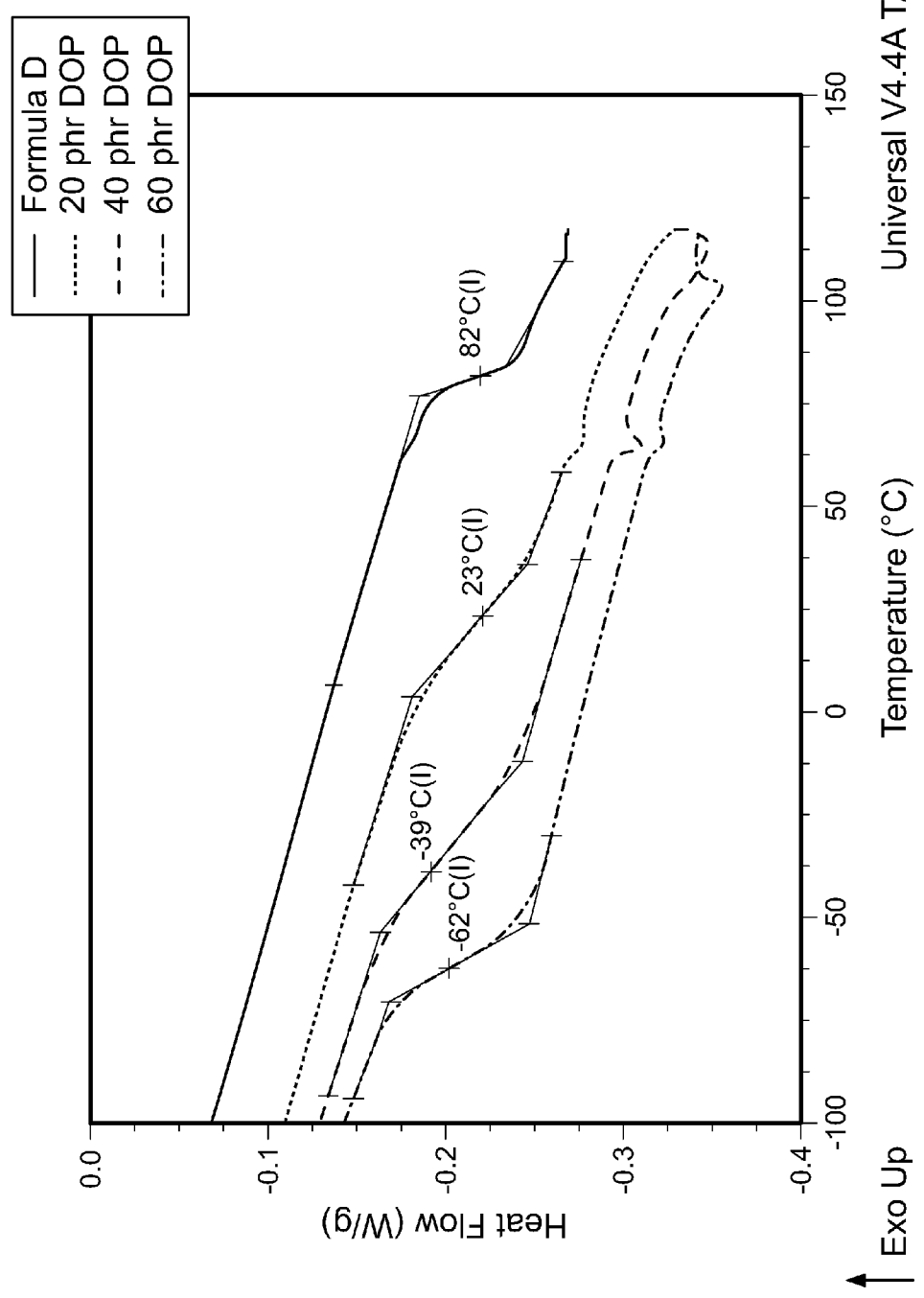
FIG. 11 depicts the glass transition temperature, Tg, of PVC and PVC compounded with DOP plasticizer at different plasticizer loadings.
Figure 12:
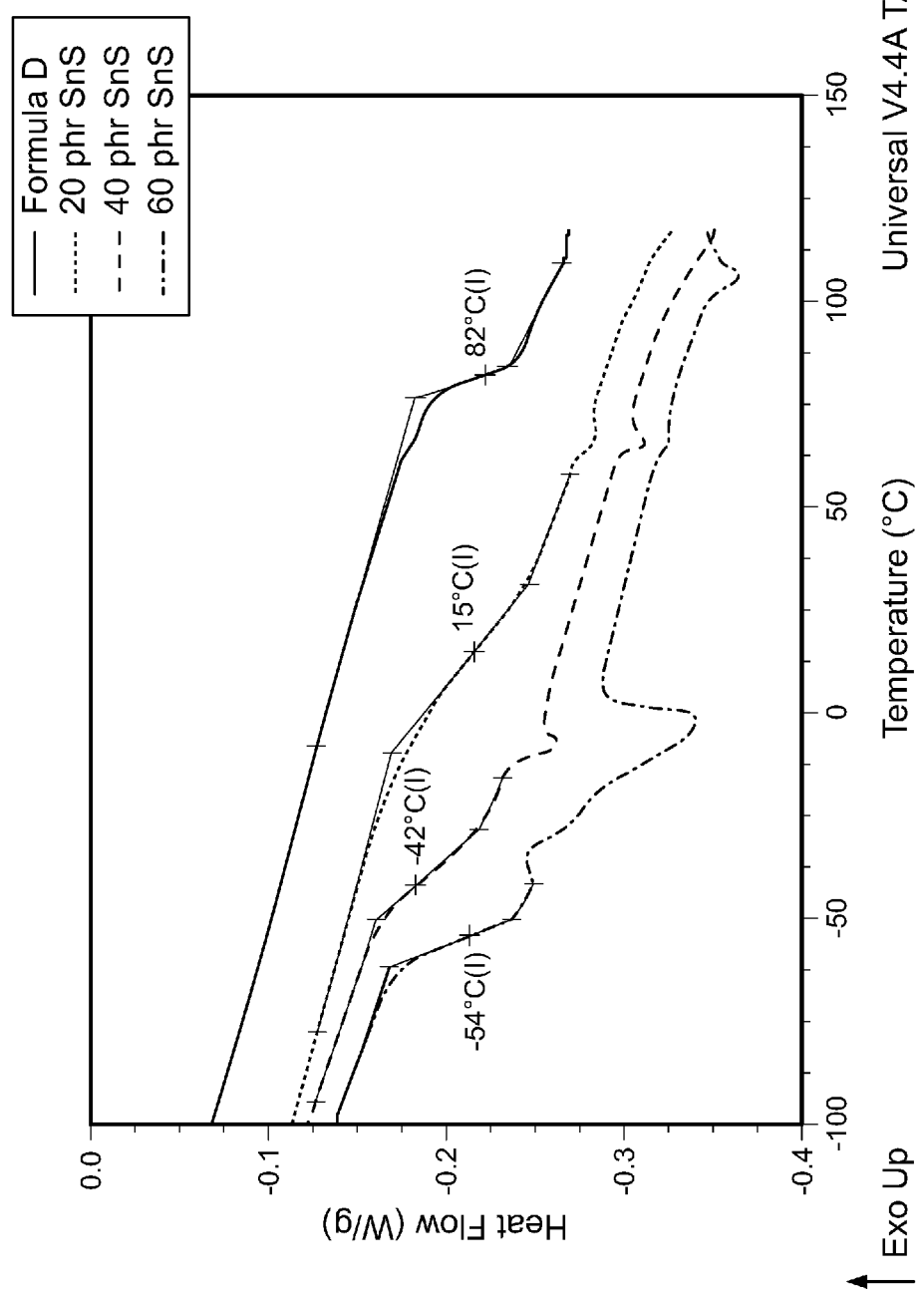
FIG. 12 the glass transition temperature, Tg, of PVC and PVC compounded with SnS plasticizer at different plasticizer loadings.
Figure 13:
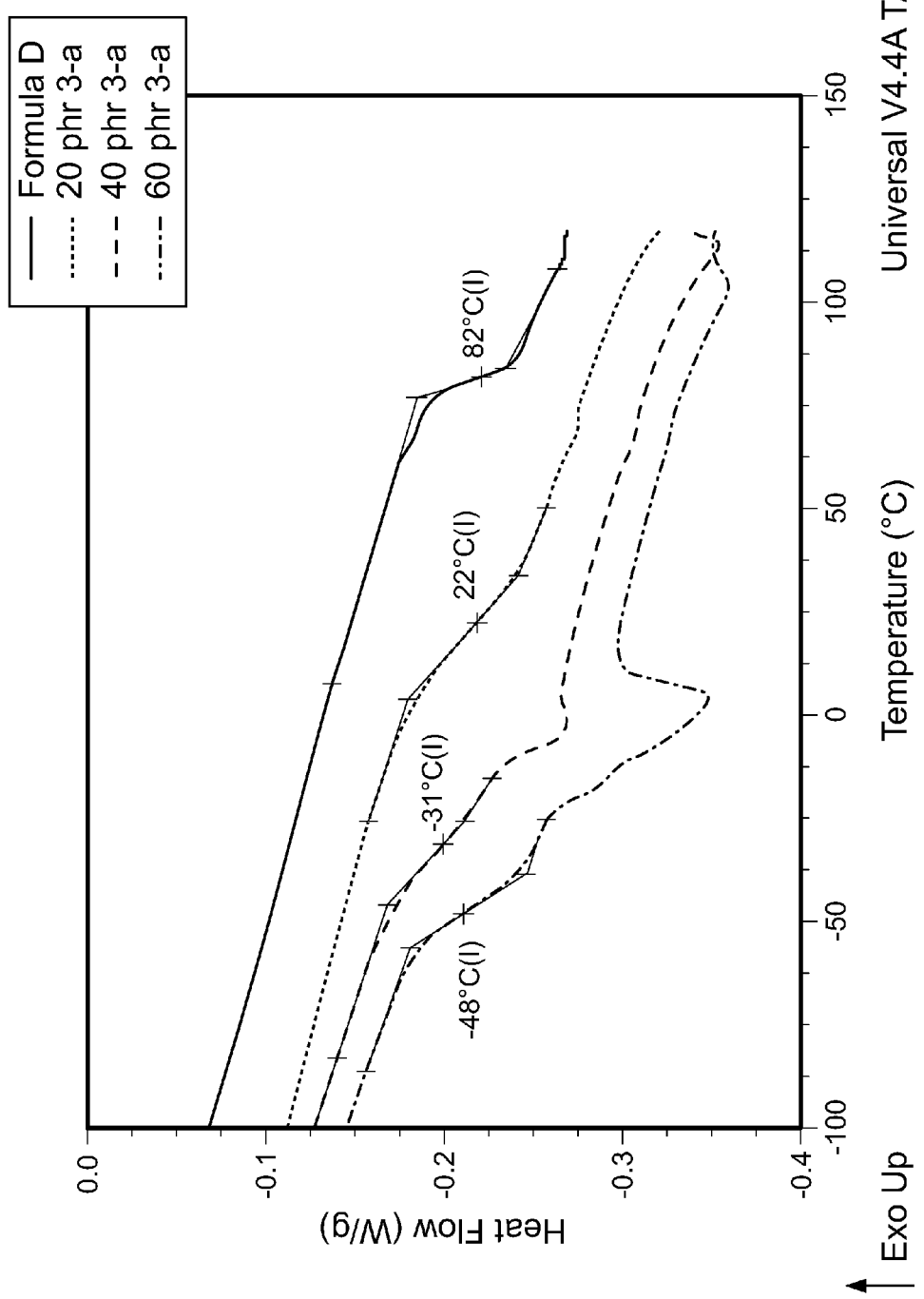
FIG. 13 depicts the glass transition temperature, Tg, of PVC and PVC compounded with plasticizer 3-a according to the invention, at different plasticizer loadings.
Figure 14:
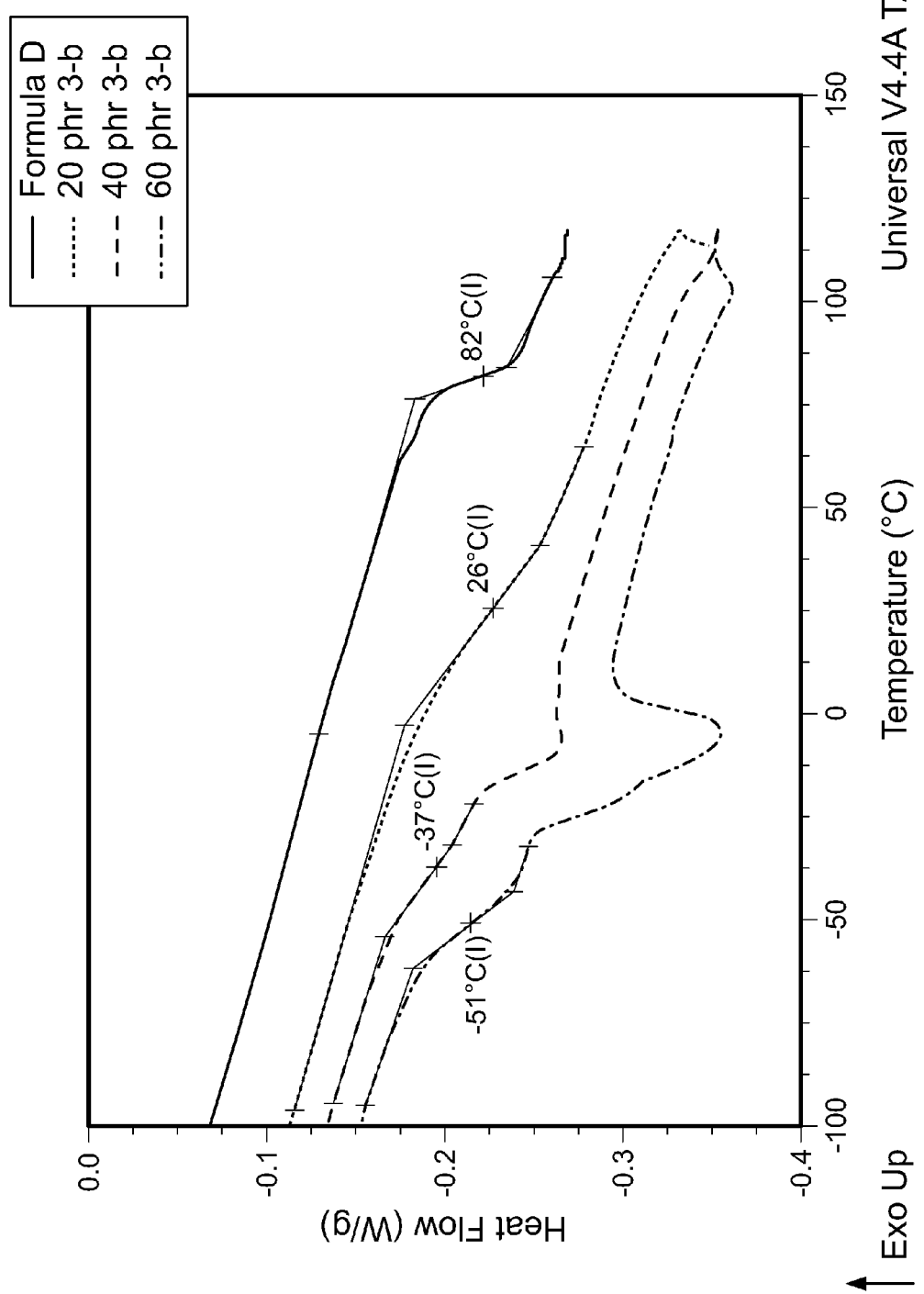
FIG. 14 depicts the glass transition temperature, Tg, of PVC and PVC compounded with plasticizer 3-b according to the invention, at different plasticizer loadings.
Figure 15:
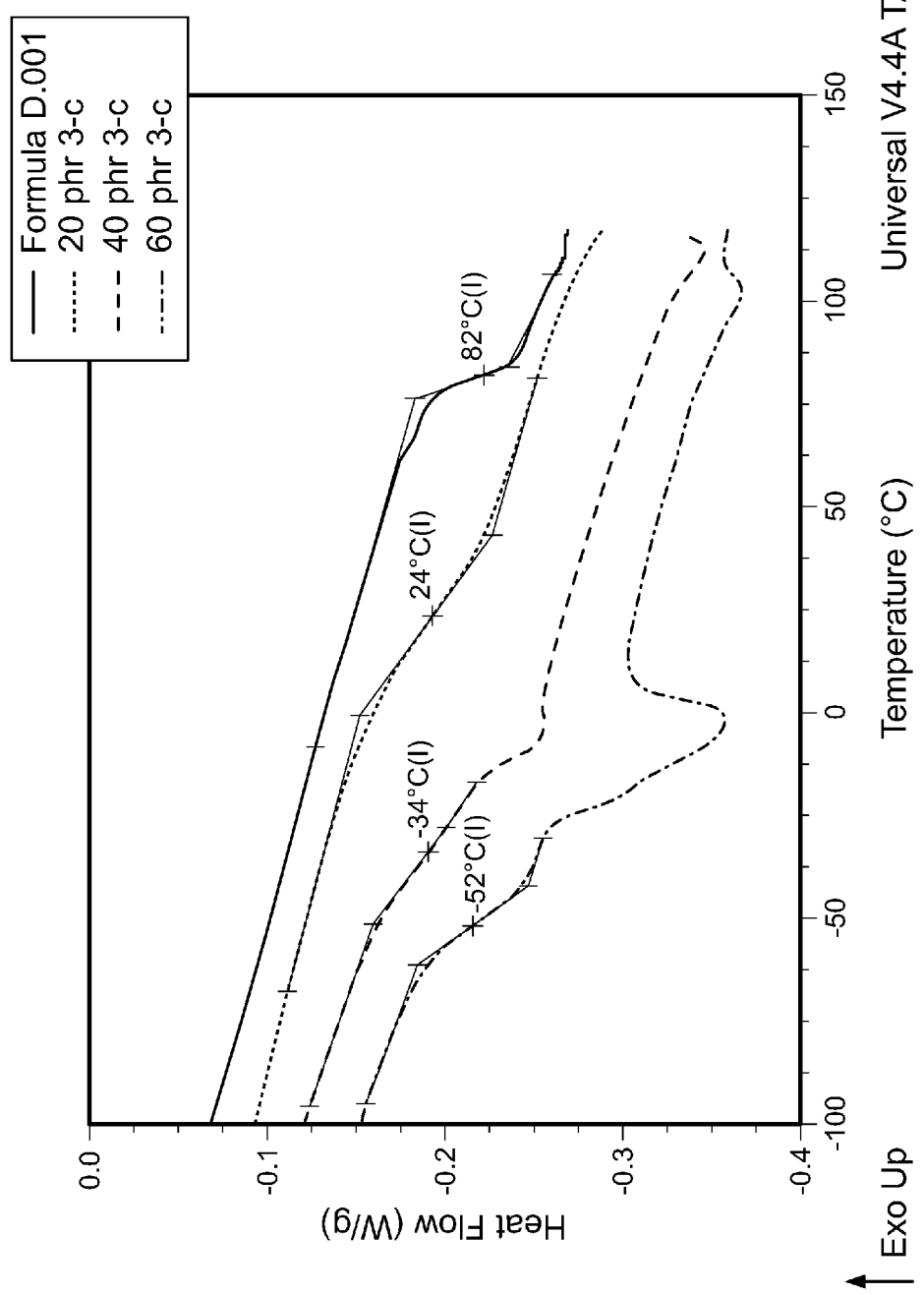
FIG. 15 depicts the glass transition temperature, Tg, of PVC and PVC compounded with plasticizer 3-c according to the invention, at different plasticizer loadings.

Thermo Gravimetric Analysis (TGA) was performed on a TA Instruments Q250 thermogravimetric analyzer with aluminum pans. Pre-weighed samples were heated at 10° C./min from ambient temperature to 500° C. The weight loss was recorded with increase in temperature (FIG. 4).

Viscosity measurements were made on a Brookfield (Boston, Mass.) model DV-E viscometer equipped with a small sample adapter using spindle number 18. The adapter was attached to a circulating water bath and maintained at constant temperature. Viscosity tests were performed according to the Brookfield model DV-E manual. The plasticizer was added to the sample chamber and allowed to equilibrate the water bath. The viscosity was measured at 100 RPM after the 5th revolution of the spindle.

Compounding of plasticizers and PVC was conducted at Aspen Research Co (Whitebear Lake, Minn.) using their Formula D PVC. Compounding was conducted on a C.W. Braebender Intelli-Torque Plastic-Corder® model: IT-7150, series: K01-123 equipped with a Prep-Mixer® model: R.E.E.6, series: 00334 fusion bowl running Winmix software. Formula D was stirred in the fusion bowl at 175° C. and 65 RPM for 6 minutes followed by the addition of the plasticizer and continued mixing at 175° C. for an additional 10 minutes. The compounded mass was removed from the fusion bowl, pressed into plastic sheets in a hydraulic press and cooled to room temperature. The plastic sheet was cut into approximately 1×1 inch pieces, cooled with liquid nitrogen and ground to a powder of <40 mesh (0.4 mm) using an analytical mill. The powder was pressed into tensile bars (ASTM D 638-04 Type V) using a mold and Carver press.

Differential Scanning calorimetry (DSC) measurements were performed on a TA Instruments DSC Q1000 modulated differential scanning calorimeter. Measurements were taken on approximately 10 mg of powdered sample sealed in non-hermetic aluminum pans. The pans were loaded into the DSC at ambient temperature and heated to 100° C. at 15° C./min; held at 100° C. for 10 min to equilibrate above the PVC glass transition temperature; cooled at 10° C./min to −150° C. The glass transition temperatures were measured by a second heating cycle from −150° C. to 120° C. heated at 10° C./min (FIGS. 11-15). The glass transition temperature was calculated using Thermal Advantage software and tabulated in Table 11.

Tensile testing was performed on an Instron (Norwood, Mass.) model 5543 equipped with a 1 kN load cell. Following ASTM D638-08, the molded Type V tensile bars were conditioned at 25° C. and 50% relative humidity for >3 days prior to testing. Tensile tests were conducted between the temperatures of 21-25° C. The bars were extended at strain rate of 0.5 in/min until the specimen ruptured. Strain and stress data were collected using Bluehill® materials testing software (Instron) and analyzed using Microsoft Excel.

Reaction Scheme I

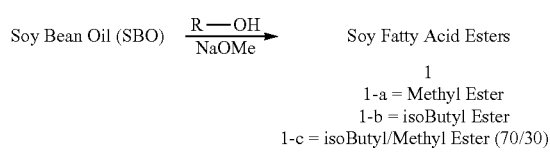

R = methyl = Soy Fatty Acid Methyl Ester (SFAME)
R = isobutyl = Soy Fatty Acid isoButyl Ester (SFABE)

Soy Fatty Acid Methyl Ester (SFAME, 1-a): aka, biodiesel is available commercially and was used as starting material for acetylated fatty acid esters.

Soy Fatty Acid Isobutyl Ester (SFABE, 1-b): A flask containing 500 g soybean oil was heated to 120° C. under vacuum for 2 hours to remove moisture. The flask was cooled to 100° C. and 6 equivalents of 2-methyl-1-propanol (isobutanol) and 0.2% sodium methoxide were added and heated to reflux. The reaction was monitored by TLC for the disappearance of the triacylglycerol spot in a 60/40 hexanes/diisopropyl ether solvent system. The reaction mixture was cooled to room temperature and transferred to a reparatory funnel. The glycerol phase was removed and the oil phase was washed 3×500 mL $H_2O$, 1×500 mL brine, and dried on $Na_2SO_4$. Excess alcohol was removed by vacuum distillation to yield 566 g Soy Fatty Acid Isobutyl Ester (SFABE, 1-b) as a light yellow oil.

Soy Fatty Acid Isobutyl/Methyl Ester (SFAB/ME, 1-c): A flask containing 500 g SFAME was heated in a 120° C. oil bath under vacuum for 2 hrs. The flask was cooled to 100° C. and 2 equivalents of 2-methyl-1-propanol (isobutanol) and 0.2% (w/w SFAME) sodium methoxide were added and heated to gentle reflux with a distillation apparatus. Isobutanol and methanol were removed at 64° C. by azeotropic distillation. The reaction end point was monitored by TLC (60/40 hexanes/diisopropyl ether solvent system) and stopped after four hours. The reaction product was cooled to 80° C. and 2% Magnesol R60 was added and allowed to cool further to room temperature before being vacuum filtered. The excess alcohol was removed by vacuum distillation to quantitatively yield Soy Fatty Acid Isobutyl/Methyl Ester (SFAB/ME, 1-c) as a mixture of 94/6 isobutyl/methyl ester. The ratio was adjusted to 70/30 isobutyl/methyl ester by the addition of excess SFAME. The 70/30 isobutyl/methyl ester ratio was also obtained by mixing SFABE and SFAME products from above.

II.

Reaction Scheme II

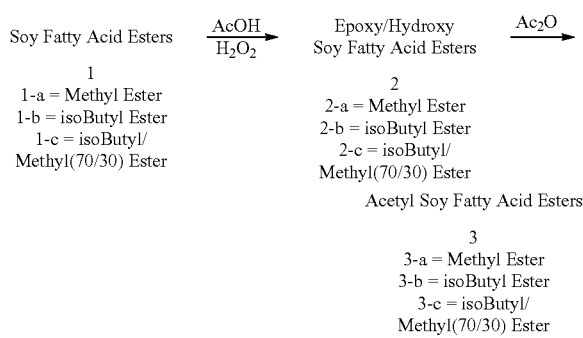

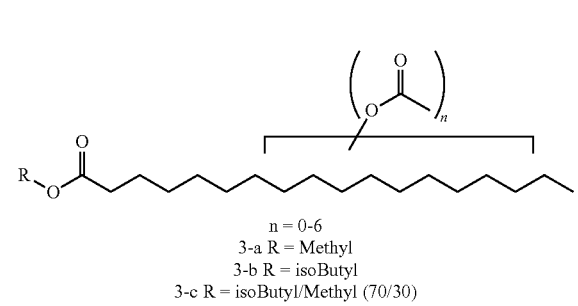

n = 0-6
3-a R = Methyl
3-b R = isoButyl
3-c R = isoButyl/Methyl (70/30)

Figure 1:
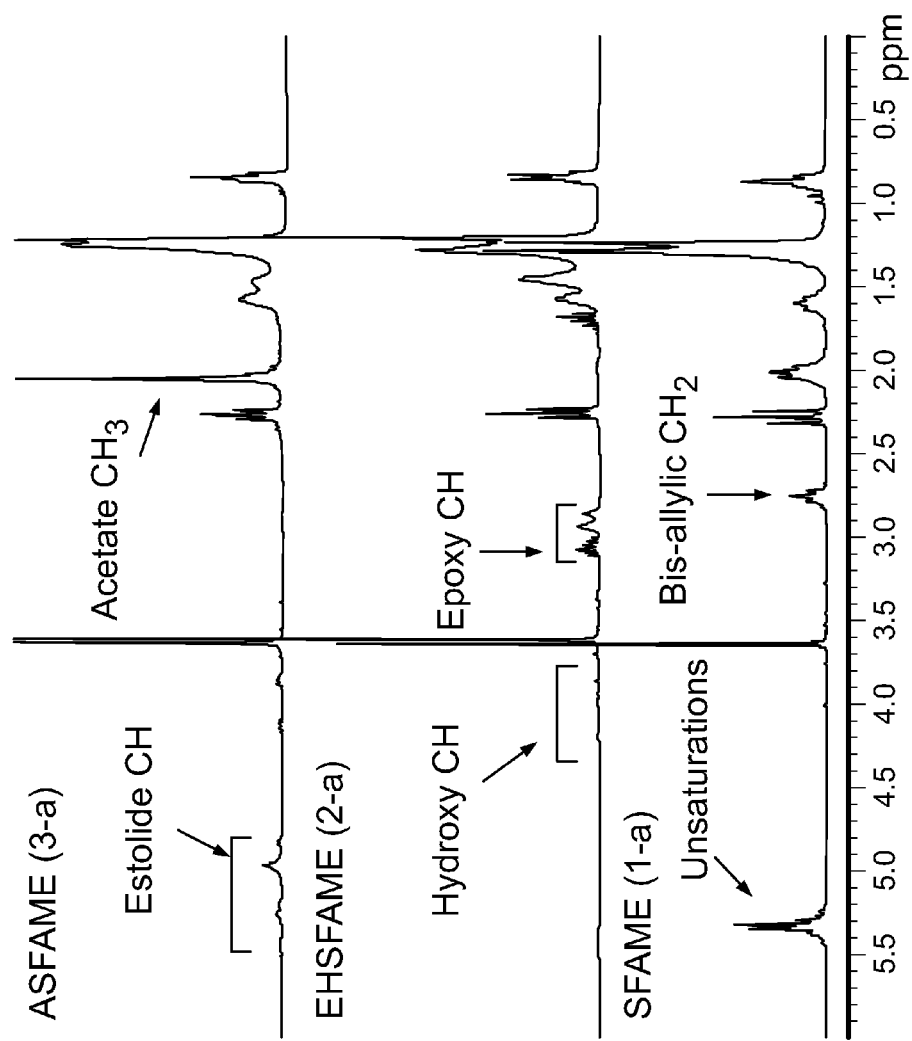
FIG. 1 depicts $^1$H NMR spectra of Soy Fatty Acid Methyl Ester (SFAME, 1-a), Epoxy/Hydroxy Soy Fatty Acid Methyl Ester (EHSFAME) (2-a), and Acetyl Soy Fatty Acid Methyl Ester (ASFAME) (3-a).
Figure 2:
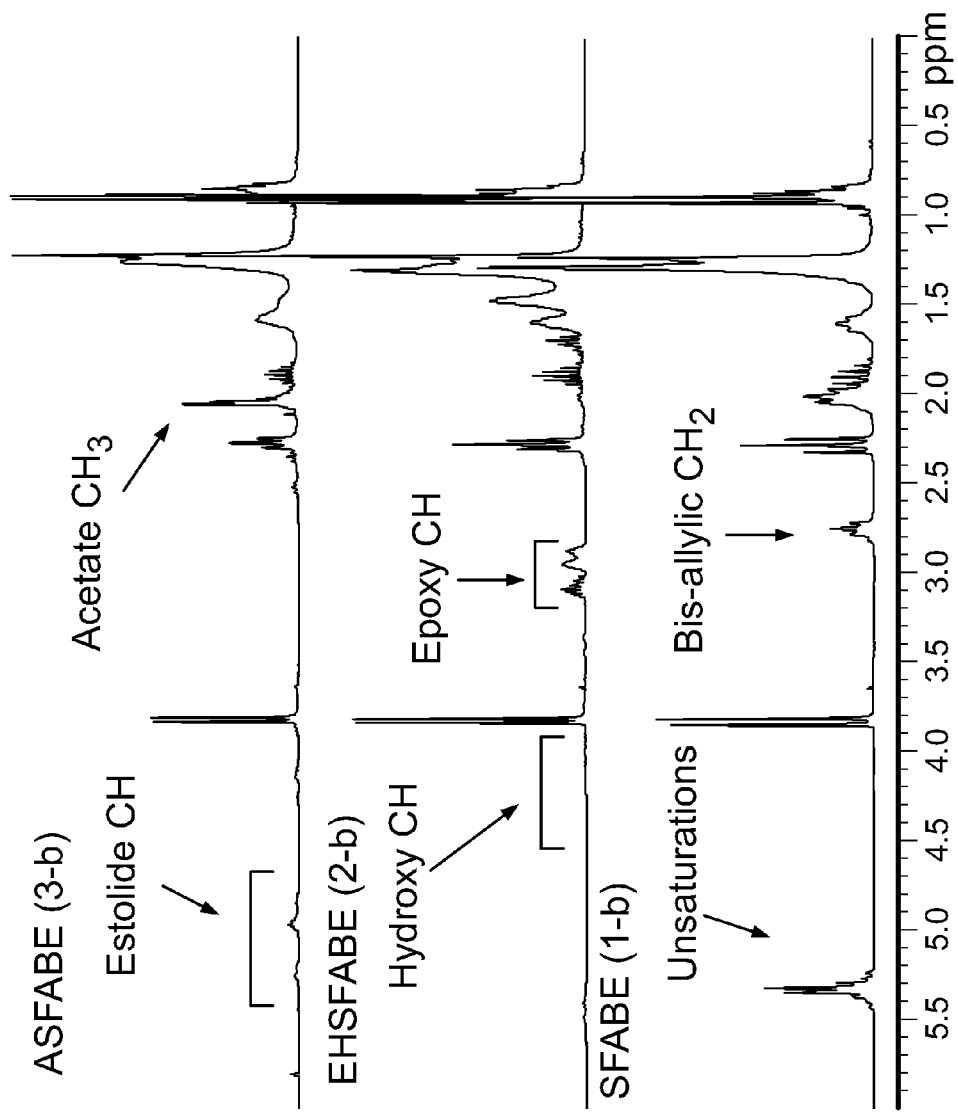
FIG. 2 depicts $^1$H NMR spectra of Soy Fatty Acid Isobutyl Ester (SFABE, 1-b), Epoxy/Hydroxy Soy Fatty Acid Isobutyl Ester (EHSFABE) (2-b), and Acetyl Soy Fatty Acid Isobutyl Ester (ASFABE) (3-b).
Figure 3:
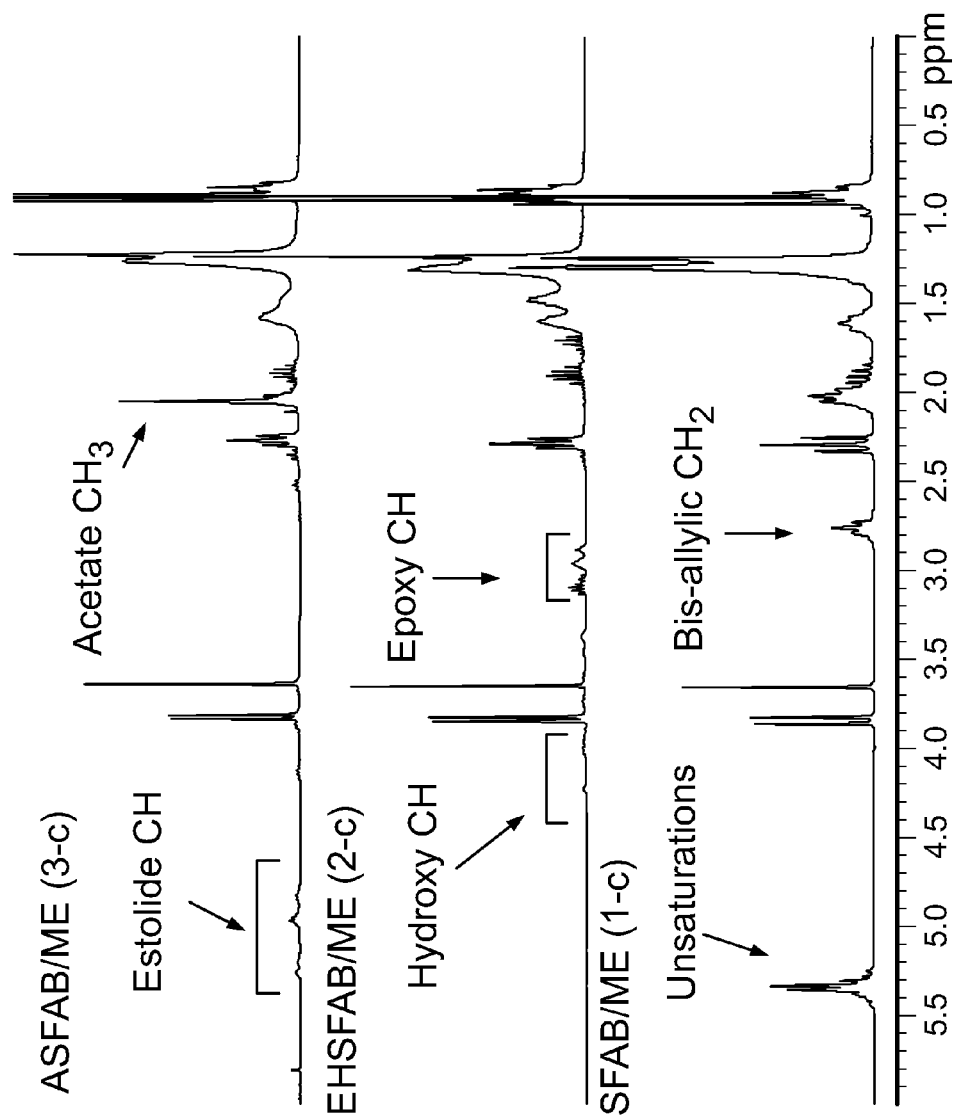
FIG. 3 depicts $^1$H NMR spectra of Soy Fatty Acid Isobutyl/Methyl Ester (SFAB/ME, 1-c), Epoxy/Hydroxy Soy Fatty Acid Isobutyl/Methyl Ester (EHSFAB/ME) (2-c), and Acetyl Soy Fatty Acid Isobutyl/Methyl Ester (ASFAB/ME) (3-c).

General Epoxidation/Hydroxylation of Soy Fatty Acid Esters (2-a to 2-c): To a flask was added 250 g soy fatty acid esters (SFAME, or SFABE, or SFAB/ME) and a mixture of 0.25 equivalents glacial acetic acid and 2% concentrated sulfuric acid while mechanically stirring (104 RPM for SFAME and 208 RPM for SFABE and SFAB/ME). To maintain the exothermic reaction below 45° C. a small portion (5%) of hydrogen peroxide (50% w/w concentration) of the total 3 equivalents per double bond was added slowly. After completion of the exothermic reaction (approximately 30 min) the remainder of the hydrogen peroxide was added slowly (in about 10 min) while maintaining the temperature around 45° C. The reaction endpoint was monitored by the complete disappearance of unsaturations, which takes 18 hours for SFAME (16 hours for SFABE and SFAB/ME). The resulting products were then transferred to a separatory funnel where the aqueous layer was removed. The organic layer was dried on $Na_2SO_4$ and vacuum filtered to quantitatively yield Epoxy/Hydroxy Soy Fatty Acid Methyl Ester (EHSFAME) (2-a), Epoxy/Hydroxy Soy Fatty Acid Isobutyl Ester (EHSFABE) (2-b), or Epoxy/Hydroxy Soy Fatty Acid Isobutyl/Methyl Ester (EHSFAB/ME) (2-c) as light yellow oils. The materials obtained were characterized by chromatography, IR, and $^1H$ NMR spectroscopy. Delta values of compounds 2-a to 2-c are listed in Table 2 and the spectra are shown in FIGS. 1-3.

Decoloring Final Products: Tests for color removal from the final products was conducted by stirring 5 g of material at 80° C. for 24 hours with 2% (w/w) of the decoloring agent, as listed in Table 4, and measured by change of Gardner Color. Sodium borohydride, all the Magnesol types, Pure-Flo, and silica gel were removed by vacuum filtration. Activated carbon was vacuum filtered through diatomaceous earth and the cocktail mixture was vacuum filtered through a plug of Magnesol® R60.

TABLE 4

Results of decoloring testing

| Decoloring Agent | Initial Color | Final Color | Color Change |
|---|---|---|---|
| Magnesol ® R60 | 13 | 13 | 0 |
| Magnesol ® 300R | 12 | 10 | −2 |
| Magnesol ® Dsol D60 | 12 | 8 | −4 |
| Magnesol ® Polysorb 30/40 | 12 | 8 | −4 |
| Pure-Flo ® B80 | 13 | 18 | +5 |

TABLE 2*

1H NMR chemical shifts of epoxy/hydroxy soy fatty acid esters, 2-a to 2-c.

| Cmpd | terminal methyl | methylene chain | methylene α to epoxy or β to carbonyl | isobutyl methine | methylene α to carbonyl | epoxy methine | ester methyl or methylene | hydroxyl methine |
|---|---|---|---|---|---|---|---|---|
| 2-a | δ 0.85, q | δ 1.23, m | δ 1.37-1.67, m | NA | δ 2.27, t | δ 2.85-3.11, m | δ 3.62, s | δ 3.30-4.20, m |
| 2-b | δ 0.87 | δ 1.26, m | δ 1.39-1.76, m | δ 1.90, m | δ 2.28, t | δ 2.89-3.82, m | δ 3.84, d | δ 3.30-4.20, m |
| 2-c | δ 0.89, m | δ 1.24, m | δ 1.39-1.72, m | δ 1.89, m | δ 2.24, t | δ 2.87-3.12, m | δ 3.62, s; δ 3.80, d | δ 3.30-4.20, m |

*s = singlet, d = doublet, t = triplet, m = multiplet

General Acetylation of Epoxy/Hydroxy Soy Fatty Acid Esters (3-a to 3-c): To a flask was added Epoxy/Hydroxy Soy Fatty Acid Ester (2-a, 2-b, or 2-c), sodium acetate (1% w/w), and acetic anhydride (2 equivalents per double bond based on original unsaturations) while magnetically stirring. The contents of the flask were reacted for three hours at 130° C. The reaction was cooled to room temperature; 200 mL hexanes were added and the contents transferred to a separatory funnel. The oil phase was extracted 3×500 mL $H_2O$, 1×500 mL 5% $NaHCO_3$, 1×500 mL Brine, dried ($Na_2SO_4$), and concentrated in vacuo to quantitatively yield Acetyl Soy Fatty Acid Methyl Ester (ASFAME) (3-a), Acetyl Soy Fatty Acid Isobutyl Ester (ASFABE) (3-b), or Acetyl Soy Fatty Acid Isobutyl/Methyl Ester (ASFAB/ME) (3-c) as brown oils (Gardner Color 12-16). The products obtained were characterized by $^1H$ NMR, IR, and chromatography. Proton NMR delta values for the final products are shown in Table 3 and in FIGS. 1-3.

TABLE 4-continued

Results of decoloring testing

| Decoloring Agent | Initial Color | Final Color | Color Change |
|---|---|---|---|
| Activated Charcoal | 13 | >18 | >5 |
| Silica Gel 60 Å | 12 | 9 | −3 |
| $NaBH_4$ | 12 | 10 | −2 |
| Cocktail Mixture (acetic acid:hydrogen peroxide:sulfuric acid, 1:2:0.1) | 12 | 8 | −4 |

TABLE 3*

1H NMR chemical shifts of acetyl soy fatty acid esters, 3-a to 3-c.

| Cmpd | terminal methyl | methylene | methylene α to acetyl or β to carbonyl | isobutyl methine | acetate methyl | methylene α to carbonyl | ester methyl or methylene | estolide methine |
|---|---|---|---|---|---|---|---|---|
| 3-a | δ 0.86, t | δ 1.26, m | δ 1.47-1.99, m | NA | δ 2.07, br s | δ 2.28, t | δ 3.64, s | δ 4.80-5.30, br m |
| 3-b | δ 0.87, m | δ 1.26, m | δ 1.37-1.59, m | δ 1.92, m | δ 2.05, br s | δ 2.27, t | δ 3.83, d | δ 4.80-5.30, br m |
| 3-c | δ 0.89, m | δ 1.25, m | δ 1.40-1.58, m | δ 1.91, m | δ 2.04, br s | δ 2.27, t | δ 3.63, s; δ 3.82, d | δ 4.80-5.30, br m |

*s = singlet, d = doublet, t = triplet, m = multiplet, br = broad

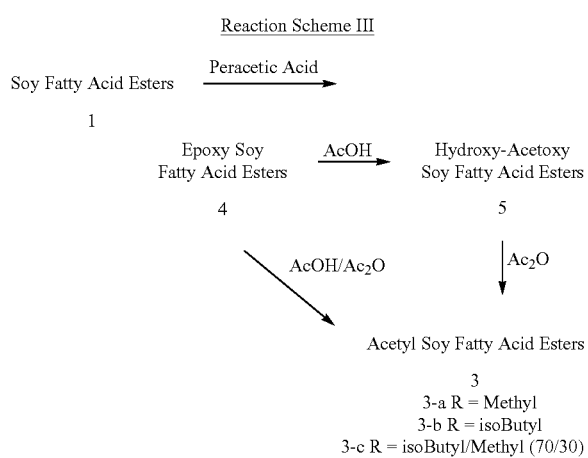

Reaction Scheme III

Acetyl Soy Fatty Acid Methyl Ester (ASFAME) (3-a)

Acetyl Soy Fatty Acid Methyl Ester (ASFAME) was obtained in a three step reaction (Reaction Scheme III). Using a reference procedure of Swern (JACS, 67(3), 1945, pp. 412) for epoxidation of fatty acid esters, 100 g of commercially available Soy Fatty Acid Methyl Ester (SFAME) was stirred at room temperature while 1.1 mol equivalents (per double bond) of 2.5 M peracetic acid in acetic acid was added at a rate to maintain the reaction temperature between 20-25° C. over a period of one hour. After the peracetic acid addition the reaction was stirred at room temperature for 9 hours. The reaction mixture was poured into a reparatory funnel containing 100 ml cold water. The water layer was removed and the organic layer was diluted with 100 ml diethyl ether and washed with 200 ml $H_2O$ twice, 200 ml 5% $NaHCO_3$ twice, 200 ml brine, dried (over $Na_2SO_4$) and filtered. The filtrate is concentrated in vacuum to quantitatively yield Epoxy Soy Fatty Acid Methyl Ester (ESFAME) as a pale yellow oil (Gardner Number 3). The product was characterized by proton NMR and IR spectra. The characteristic protons for the epoxy methines fell between δ 2.8 and δ 3.1 in proton NMR as seen in Table 5.

In the second step, 40 g of the above ESFAME was reacted at 130° C. with 1.2 mol (per original double bond) acetic acid for 5.5 hours. The reaction mixture was cooled to room temperature, diluted with 10 ml hexanes, washed with 80 ml $H_2O$ thrice, 80 ml 5% $NaHCO_3$, 80 ml brine, dried (over $Na_2SO_4$), and concentrated in vacuum to quantitatively yield Hydroxy/Acetoxy Soy Fatty Acid Methyl Ester (HASFAME) as a yellow/brown oil (Gardner Number 11). Characterization by proton NMR and IR spectroscopy confirmed the presence of hydroxy methines between δ 3.3 and δ 4.0 in NMR and a strong OH transmission peak around 3400 $cm^{-1}$ in IR. An acetyl methyl peak is also observed at δ 2.0 in NMR confirming the formation of hydroxy-acetoxy moiety at the site of unsaturation as seen in Table 5.

In the third step, 2 g of HASFAME was reacted at 130° C. with 0.7 equivalents (per original double bond) acetic anhydride for 6 hours. The reaction mixture was cooled to room temperature, diluted with 2 ml hexanes, washed with 5 ml $H_2O$ thrice, 5 ml 5% $NaHCO_3$, 5 ml brine, dried (over $Na_2SO_4$), and concentrated in vacuum to quantitatively yield Acetyl Soy Fatty Acid Methyl Ester (ASFAME) as a yellow oil (Gardner Number 8). Characterization by proton NMR and IR spectroscopy confirmed the structure of a fully acetylated soy fatty acid ester having approximately 1.6 acetyl groups per fatty acid ester. The number of acetyl groups was determined by the integration value of the acetyl peak at δ 2.01 relative to the methyl group of the fatty acid ester at δ 0.85. Proton NMR δ-values are tabulated in Table 5.

ASFAME can also be obtained in a two step reaction (Reaction Scheme III) by first reacting 100 g of SFAME with peracetic acid, as in example 1, to produce ESFAME. In the second step 100 g of ESFAME was reacted at 130° C. with 1.2 equivalents (per original double bond) acetic acid and 0.75 equivalents (per original double bond) acetic anhydride for 5 hours. The mixture was cooled to room temperature, diluted with 100 ml hexanes, washed with 200 ml H2O thrice, 200 ml 5% NaHCO3 twice, 200 ml brine, dried (over Na2SO4), filtered, and concentrated in vacuum to quantitatively yield ASFAME as a brown oil (Gardner Number 12). Characterization by proton NMR and IR spectra as in the previous example confirms the structure of a fully acetylated fatty acid methyl ester having approximately 1.6 acetyl groups per fatty acid ester. Proton NMR δ-values are tabulated in Table 5.

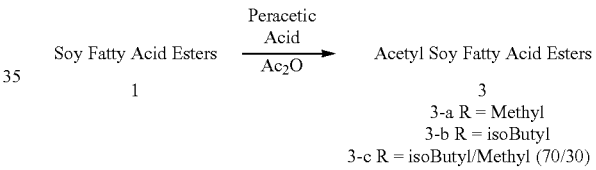

Reaction Scheme IV

ASFAME was also obtained in a one pot reaction (Reaction Scheme IV) by epoxidizing 2 g SFAME with peracetic acid as in the previous examples. After 15 hours reacting at room temperature the temperature was increased to 130° C. and further reacted for an additional 1.25 hours when 1 equivalent (per double bond) acetic anhydride was added and further reacted for 3 hours. The reaction mixture was cooled to room temperature, diluted with 2 ml hexanes, washed 3×5 ml $H_2O$, 1×5 ml 5% $NaHCO_3$, 1×5 ml brine, dried ($Na_2SO_4$), filtered, and concentrated in vacuum to quantitatively yield ASFAME as a brown oil (Gardner Number 15-16). Characterization of the product by proton NMR and IR spectra confirmed the structure of a fully acetylated soy fatty acid methyl ester having approximately 1.8 acetyl groups per fatty acid ester. Proton NMR δ-values are tabulated in Table 5.

TABLE 5*

1H NMR chemical shifts of Soy Fatty Acid Methyl Esters (SFAME), Epoxy Soy Fatty Acid Methyl Esters (ESFAME), Hydroxy/Acetoxy Soy Fatty Acid Methyl Esters (HASFAME), and Acetyl Soy Fatty Acid Methyl Esters (ASFAME).

| Cmpd | terminal methyl | methylene chain | methylene β to carbonyl | bis epoxy methylene | methylene α to double bond, epoxy, or acetyl | acetate methyl | methylene α to carbonyl | bis allylic methylene, or epoxy methine | ester methyl | hydroxyl methine | double bond methine or estolide methine |
|---|---|---|---|---|---|---|---|---|---|---|---|
| SFAME | δ 0.86, m | δ 1.24, m | δ 1.60, m | NA | δ 2.01, m | NA | δ 2.28, t | δ 2.75, m | δ 3.62, s | NA | δ 5.27-5.37, m |

TABLE 5*-continued

1H NMR chemical shifts of Soy Fatty Acid Methyl Esters (SFAME), Epoxy Soy Fatty Acid Methyl Esters (ESFAME), Hydroxy/Acetoxy Soy Fatty Acid Methyl Esters (HASFAME), and Acetyl Soy Fatty Acid Methyl Esters (ASFAME).

| Cmpd | terminal methyl | methylene chain | methylene β to carbonyl | bis epoxy methylene | methylene α to double bond, epoxy, or acetyl | acetate methyl | methylene α to carbonyl | bis allylic methylene, or epoxy methine | ester methyl | hydroxyl methine | double bond methine or estolide methine |
|---|---|---|---|---|---|---|---|---|---|---|---|
| ESFAME | δ 0.87, m | δ 1.23, m | δ 1.61, m | δ 1.74, m | δ 1.50–1.61, m | NA | δ 2.22, t | δ 2.79–3.05, m | δ 3.57, s | NA | NA |
| HASFAME | δ 0.83, m | δ 1.25, m | δ 1.56, m | NA | δ 1.35–1.56, m | δ 2.04, m | δ 2.25, t | NA | δ 3.1, s | δ 3.30–4.00, m | NA |
| ASFAME | δ 0.80, m | δ 1.21, m | δ 1.54, m | NA | δ 1.53, m | δ 2.01, br s | δ 2.23, t | NA | δ 3.59, s | NA | δ 4.80–5.40, m |

*s = singlet, d = doublet, t = triplet, m = multiplet

Acetyl Soy Fatty Acid Isobutyl Ester (ASFABE) (3-b)

ASFABE was obtained in a two step reaction from previously made SFABE. In the first step 100 g SFABE was stirred at room temperature while 1.1 equivalents (per double bond) peracetic acid in acetic acid was added at a rate to maintain the reaction temperature between 20-25° C. The reaction was stirred at room temperature for 14.5 hours. The reaction mixture was poured into a separatory funnel containing 200 ml cold water. The aqueous phase was removed and the organic phase was diluted with 50 ml diethyl ether, washed 100 ml $H_2O$ twice, 100 ml 5% $NaHCO_3$ twice, 100 ml brine, dried (over $Na_2SO_4$), filtered, and concentrated in vacuum to yield 75 g of Epoxy Soy Fatty Acid isoButyl Ester (ESFABE) as a pale oil (Gardner Number 2-3). Characterization of the product by proton NMR and IR spectra confirm the structure of a fully epoxidized soy fatty acid ester as seen in table 6. The characteristic epoxy methine peaks were observed in proton NMR between δ 2.8 and δ 3.1 as can be seen in Table 6.

In the second step, 100 g of ESFABE was reacted at 130° C. with 1.2 equivalents (per original double bond) acetic acid and 0.75 equivalents (per original double bond) acetic anhydride for 5 hours. The reaction mixture was cooled to room temperature, diluted with 100 ml hexanes, washed with 250 ml $H_2O$ thrice, 250 ml 5% $NaHCO_3$, 250 ml brine, dried (over $Na_2SO_4$), filtered, and concentrated in vacuum to quantitatively yield ASFABE as a yellow/brown oil (Gardner Number 10). Characterization of the product by proton NMR and IR spectra confirmed the structure of a fully acetylated soy fatty acid ester having approximately 2.0 acetyl groups per fatty acid ester. The characteristic proton NMR δ-values of the compounds are tabulated in Table 6.

Reaction Scheme V

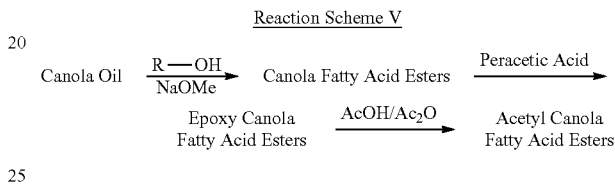

Acetyl Canola Fatty Acid Methyl Esters (ACFAME)

Acetyl Canola Fatty Acid Methyl Esters can be obtained in a three step reaction from commercially available canola oil (Reaction Scheme V). In the first step 300 g canola oil is dried under vacuum at 120° C. overnight to remove moisture. After cooling to 50° C., 7 equivalents anhydrous methanol and 0.2% w/w sodium methoxide were added under an inert atmosphere. The mixture was heated to reflux and monitored by TLC for the disappearance of the triacylglycerol spot in a 60/40 hexanes/diisopropyl ether solvent system (approximately 3 hours). While the reaction mixture was still hot the glycerol layer was removed and 2% Magnesol Polysorb 30/40 was added. After cooling to room temperature the contents were filtered under vacuum. Excess alcohol was removed by vacuum distillation to quantitatively yield Canola Fatty Acid Methyl Ester (CFAME) as a yellow oil. The product was characterized by proton NMR and IR spectroscopy and is tabulated in table 7.

In the second step 100 g CFAME was stirred at room temperature while 1.1 equivalents (per double bond) peracetic acid in acetic acid was added at a rate to maintain the reaction temperature between 20-25° C. The reaction was

TABLE 6*

1H NMR chemical shifts of Soy Fatty Acid isobutyl Esters (SFABE), Epoxy Soy Fatty Acid isobutyl Esters (ESFABE), and Acetyl Soy Fatty Acid isobutyl Esters (ASFABE).

| Cmpd | terminal methyl | methylene chain | methylene β to carbonyl | isobutyl methine | bis epoxy methylene | methylene α to double bond, epoxy, or acetyl | acetate methyl | methylene α to carbonyl | bis allylic methylene, or epoxy methine | ester methylene | hydroxyl methine | double bond methine or estolide methine |
|---|---|---|---|---|---|---|---|---|---|---|---|---|
| SFABE | δ 0.86, m | δ 1.24, m | δ 1.61, m | δ 1.90, m | NA | δ 2.06, m | NA | δ 2.29, t | δ 2.75, m | δ 3.82, d | NA | δ 5.24–5.40, m |
| ESFAB1 | δ 0.88, m | δ 1.23, m | δ 1.61, m | δ 1.90, m | δ 1.71, m | δ 1.58, m | NA | δ 2.22, t | δ 2.83–3.10, m | δ 3.79, d | NA | NA |
| ASFAB1 | δ 0.87, m | δ 1.25, m | δ 1.54, m | δ 1.88, m | NA | δ 1.54, m | δ 2.04, br s | δ 2.26, t | NA | δ 3.79, d | NA | δ 4.75–5.28, m |

*s = singlet, d = doublet, t = triplet, m = multiplet stirred at room temperature for 12 hours. The reaction mixture was poured into a reparatory funnel containing 200 ml cold water. The aqueous phase was removed and the organic phase was diluted with 50 ml diethyl ether, washed 100 ml $H_2O$ twice, 100 ml 5% $NaHCO_3$ twice, 100 ml brine, dried (over $Na_2SO_4$), filtered, and concentrated in vacuum to yield 95 g of Epoxy Canola Fatty Acid Methyl Ester (ECFAME) as a pale yellow oil (Gardner Number 2-3). Characterization of the product by proton NMR and IR spectra confirm the structure of a fully epoxidized canola fatty acid ester. The characteristic epoxy methine peaks were observed in proton NMR between δ 2.8 and δ 2.9 as can be seen in Table 7.

In the third step, 10 g of ECFAME was reacted at 130° C. with 1.2 equivalents (per original double bond) acetic acid and 0.75 equivalents (per original double bond) acetic anhydride for 6.5 hours. The reaction mixture was cooled to room temperature, diluted with 10 ml hexanes, washed with 25 ml $H_2O$ thrice, 25 ml 5% $NaHCO_3$, 25 ml brine, dried (over $Na_2SO_4$), filtered, and concentrated in vacuum to quantitatively yield Acetyl Canola Fatty Acid Methyl Ester (ACFAME) as a light brown oil (Gardner Number 11-12). The product was characterized by proton NMR and IR spectroscopy and the δ-values are tabulated in table 7. The acetylated product contained approximately 1.2 acetyl groups per fatty acid ester.

TABLE 7*

1H NMR chemical shifts of Canola Fatty Acid Methyl Ester (CFAME), Epoxy Canola Fatty Acid Methyl Ester (ECFAME), and Acetyl Canola Fatty Acid Methyl Ester (ACFAME).

| Cmpd | terminal methyl | methylene chain | methylene β to carbonyl | bis epoxy methylene | methylene α to double bond, epoxy, or acetyl | acetate methyl | methylene α to carbonyl | bis allylic methylene, or epoxy methine | ester methyl | hydroxyl methine | double bond methine or estolide methine |
|---|---|---|---|---|---|---|---|---|---|---|---|
| CFAME | δ 0.86, m | δ 1.25, m | δ 1.60, m | NA | δ 1.98, m | NA | δ 2.28, t | δ 2.75, m | δ 3.64, s | NA | δ 5.30-5.37, m |
| ECFAME | δ 0.83, m | δ 1.27, m | δ 1.59, m | δ 1.68, m | δ 1.44, m | NA | δ 2.23, t | δ 2.84-2.93, m | δ 3.61, s | NA | NA |
| ACFAME | δ 0.83, m | δ 1.21, m | δ 1.57, m | NA | δ 1.45, m | δ 2.04, br s | δ 2.25, t | NA | δ 3.63, s | NA | δ 4.73-5.49, m |

*s = singlet, d = doublet, t = triplet, m = multiplet

Plasticizer Evaluation

The characterization and physical properties of the plasticizers prepared according to Reaction Scheme II were conducted according to standardized methods from the American Oil Chemists Society or the American Society for Testing and Materials, and are tabulated in Table 8. Characterization of volatility for the experimental and commercial plasticizers was conducted using TGA and is shown in FIG. 4 with the onset of weight loss for the plasticizers tabulated in Table 9.

TABLE 8

Plasticizer physical properties.

| | | Plasticizer | | | | |
|---|---|---|---|---|---|---|
| Property | Test Method | DOP Exp. (Lit.) | Soft-N-Safe Exp. (Lit.) | 3-a | 3-b | 3-c |
| Acid Value (mg KOH/g) | AOCS Cd 3d-63 | 0.11 (0.005)[1] | 0.36 (<3)[2] | 2.94 | 3.18 | 2.27 |
| Saponification Value (mg KOH/g) | AOCS Cd 3-25 | NA | 419 (~435)[2] | 367 | 314 | 319 |
| Oxirane Oxygen (%) | ASTM: D-1652-04 | NA | NA | 0.22 | 0.03 | 0.01 |
| Hydroxyl Value (mg KOH/g) | AOCS Cd 13-60 | NA | NA | 5.6 | 1.5 | 3.5 |
| Color (Gardner Number) | ASTM: D1544-04 | 1 (15)[1,3] | 1 (clear liquid)[2] | 8 | 8 | 8 |
| Viscosity (cP) @ 25° C. (Brookfield) | | 66.9 (56)[1] | 118.7 (106)[2] | 113 | 109 | 87 |

[1] Eastman DOP Plasticizer technical data sheet
[2] Soft-n-Safe brochure
[3] Platinum-Cobalt scale
onset of weight loss for the plasticizers tabulated in Table 9.

TABLE 9

Onset of Weight Loss of Plasticizers

| Plasticizer | Temperature (° C.) |
|---|---|
| DOP | 225 |
| Soft-N-Safe | 249 |
| 3-a | 207 |
| 3-b | 210 |
| 3-c | 230 |

Evaluation of Plasticizers Compounded with PVC

The experimental plasticizers prepared according to Reaction Scheme II were evaluated and compared to commercial plasticizers DOP and SnS (Soft-N-Safe plasticizer from Danisco) by compounding with Formula D at concentrations of 20, 40, and 60 phr. After compounding, plastic sheets were hydraulically pressed and cut into ~1×1 inch pieces. The pieces were frozen with liquid nitrogen and cryogenically ground with an analytical mill into a powder of <40 mesh (0.4 mm). The powder was pressed into ASTM D638-08 Type V tensile bars using a mold and Carver press. The temperatures used for pressing were 180, 160, and 140° C. for plasticizer concentrations of 20, 40, and 60 phr respectively. The tensile properties were evaluated according to the ASTM procedure and plotted in FIGS. 5-10 with the results tabulated in Table 10.

TABLE 10

Tensile property comparisons of plasticized PVC with commercial and experimental plasticizers.

| Concentration (phr) | Plasticizer | Tensile Strength at Break (Mpa) | 100% Modulus (Mpa) | Elongation (%) |
|---|---|---|---|---|
| 20 | DOP | 28.6 | 26.0 | 139.0 |
|  | SnS | 26.0 | 22.5 | 153.3 |
|  | 3-a | 26.5 | 25.3 | 113.9 |
|  | 3-b | 27.0 | 26.9 | 104.7 |
|  | 3-c | 29.1 | 26.6 | 146.1 |
| 40 | DOP | 12.2 | 5.0 | 381.9 |
|  | SnS | 14.1 | 5.2 | 449.9 |
|  | 3-a | 12.9 | 5.2 | 393.8 |
|  | 3-b | 13.4 | 6.6 | 311.0 |
|  | 3-c | 14.5 | 6.5 | 342.5 |
| 60 | DOP | 3.6 | 1.5 | 358.3 |
|  | SnS | 5.0 | 1.9 | 405.2 |
|  | 3-a | 3.9 | 1.9 | 279.6 |
|  | 3-b | 5.1 | 2.0 | 367.3 |
|  | 3-c | 3.0 | 2.0 | 182.7 |

Change in glass transition temperature (Tg) for the powders compounded with the plasticizers at various concentrations was measured using DSC. Glass transition temperatures for PVC and the plasticized PVC are shown in FIGS. 11-15 and tabulated in Table 11.

TABLE 11

Glass Transition Temperature (Tg) of PVC with Different Plasticizer Loading

| Plasticizer Loading (phr) | Tg midpoint (° C.) | | | | | |
|---|---|---|---|---|---|---|
| | Formula D | DOP | Soft-N-Safe | 3-a | 3-b | 3-c |
| 0 | 82 | — | — | — | — | — |
| 20 | — | 23 | 15 | 22 | 26 | 24 |
| 40 | — | −39 | −42 | −31 | −37 | −34 |
| 60 | — | −62 | −54 | −48 | −51 | −52 |

Reaction Scheme VI

Reaction Scheme VI is similar to Reaction Scheme I except that instead of using sulfuric acid as a catalyst for the epoxidation of the fatty acid methyl esters, Amberlite IR 120 H+ form ion exchange resin is used as the catalyst. Because this resin because is a heterogeneous catalysis, it can be easily separated from the reaction mixture and reused several times. In addition, by using the resin instead of $H_2SO_4$, the epoxidation is complete without any side reactions of ring opened hydroxy compounds. Specific reaction details are set forth below.

Epoxidized Soy Fatty Acid Methyl Esters (EFAME)

A baffled reactor equipped with mechanical stirring and a reflux condenser was charged with 2.5 kg Soy Fatty Acid Methyl Ester (Soy FAME), 377 ml (0.5 mol per double bond) of acetic acid, 835 ml (1.1 mol per double bond) of 50% $H_2O_2$, and 125 g (5 wt % Soy FAME) of dried Amberlite IR 120 H+ ion exchange resin. The flask was stirred at 1000 RPM and heated to 60° C. The heat was removed and the exothermic reaction was allowed to further heat the reaction mixture to 75° C. The reaction temperature was maintained at 75° C. with external cooling for 1 hour followed by external heating for an additional 6 hours. The reaction mixture was filtered under vacuum and allowed to separate into two layers. The aqueous layer was removed and the organic layer was vacuum distilled to remove excess acetic acid. The distilled material was stirred with 2% Magnesol and filtered under vacuum to yield 110% epoxy fatty acid methyl ester (EFAME) as a pale yellow oil (Gardner Number 1). The product was characterized by NMR and IR spectra. The characteristic protons for epoxy methines were observed at δ 2.8 and δ 3.1 in proton NMR.

Acetyl Fatty Acid Methyl Esters (AFAME)

To a flask equipped with a reflux condenser containing 2.0 kg Epoxidized Soy Fatty Acid Methyl Esters (EFAME) was added glacial acetic acid (1.85 mol), and acetic anhydride (1.16 mol) and the flask was heated to 130° C. while magnetically stirring. After reacting for 5 hours the contents of the flask were cooled to room temperature where excess acetic anhydride was allowed to react with $H_2O$ (5% w/w EFAME) for 30 minutes followed by the addition of $H_2O_2$ (4% w/w EFAME) (59% w/w $H_2O$) and allowed to bleached for 3 days at room temperature. The acetic acid and $H_2O_2$ were removed by vacuum distillation to yield Acetylated Soy Fatty Acid Methyl Esters (AFAME) as light yellow colored oil (Gardner Number 1).)

Figure 16:
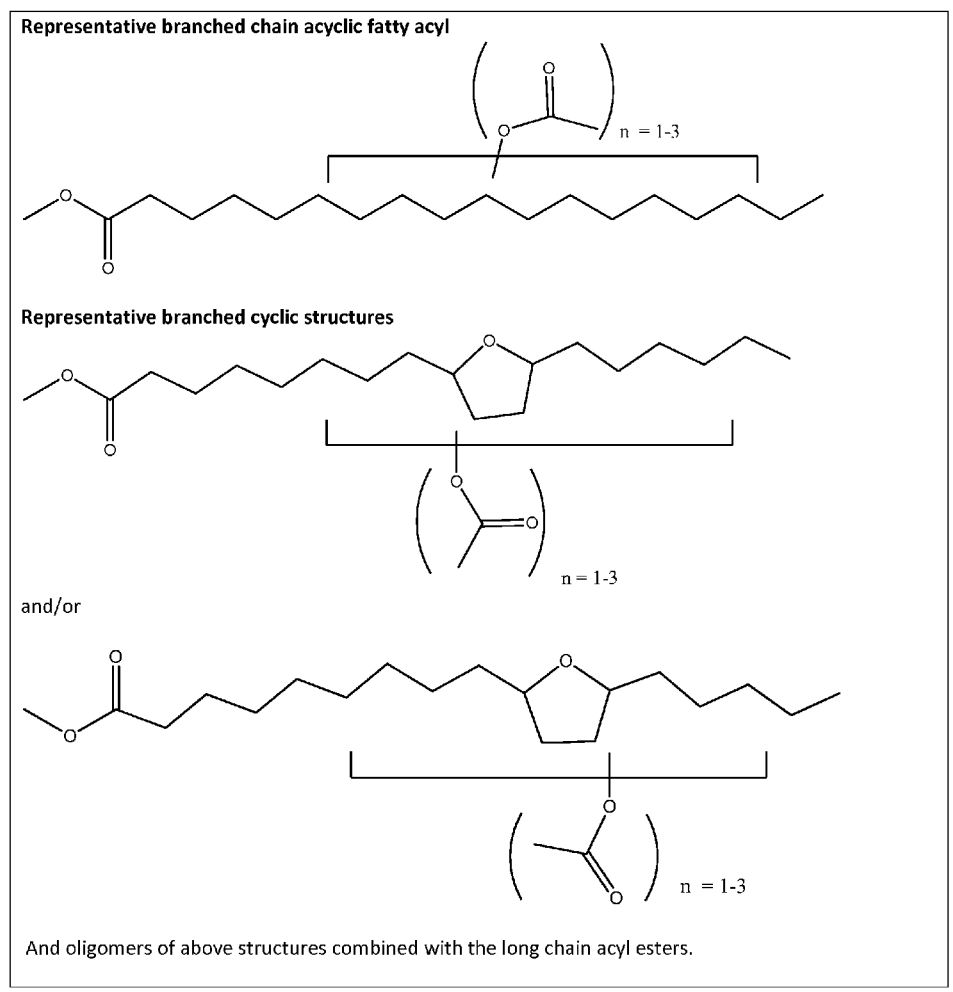
FIG. 16 is an illustration of the structures of acetylated soy fatty acid methyl esters (AFAME) prepared according to Reaction Scheme VI.

The final product, AFAME, was evaluated using column chromatography to separate the different structural moieties and analyzing them using $^1$H NMR, GC, and GC-MS. A summary of the components, their percent composition and some of their properties are tabulated in Table 12 and Table 13. The data in Tables 12 and 13 reflects the fractionation results of two separate samples (LJS 272 and LJS 341). It was found that the composition was composed of saturated fatty acid methyl esters, acyclic branched fatty acid methyl esters, cyclic branched fatty acid methyl esters and oligomers of the above methyl esters. The structures of the acyclic and cyclic branched moieties are shown in FIG. 16.

TABLE 12

Column components of AFAME
AFAME Column 1: LJS-272

| Fraction | Wt % | Ave. Acetyl # | Description | Comment |
|---|---|---|---|---|
| I | 7.5 | 0 | White solid | Saturated esters |
| II | 10.9 | 0.92 | Clear liq | Acyclic branched |
| III | 21.4 | 1.86 | Clear liq | Mostly acyclic branched |
| IV | 27.6 | 1.56 | Clear liq | Cyclic branched |
| V | 9.4 | 2.43 | Clear liq | |
| VI | 2.0 | 2.28 | Clear liq | |
| VII | 21.2 | 2.27 | Dark visc liq | Oligomeric esters |

TABLE 13

Column components of AFAME
AFAME Column 2: LJS-341

| Fraction | Wt % | Ave. Acetyl # | Description | Comment |
|---|---|---|---|---|
| I | 10.6 | 0 | White solid | Saturated esters |
| II | 17.0 | 1.98 | Yellow liq | Acyclic diacetates |
| III | 5.0 | 1.66 | Yellow liq | Mixture acyclic/cyclic branched |
| IV | 32.7 | 2.40 | Yellow liq | Cyclic branched |
| V | 6.5 | 1.87 | Yellow liq | |
| VI | 4.1 | 2.09 | Yellow liq | |
| VII | 24.1 | 2.14 | Dark visc liq | Oligomeric esters of above materials |

Figure 17:
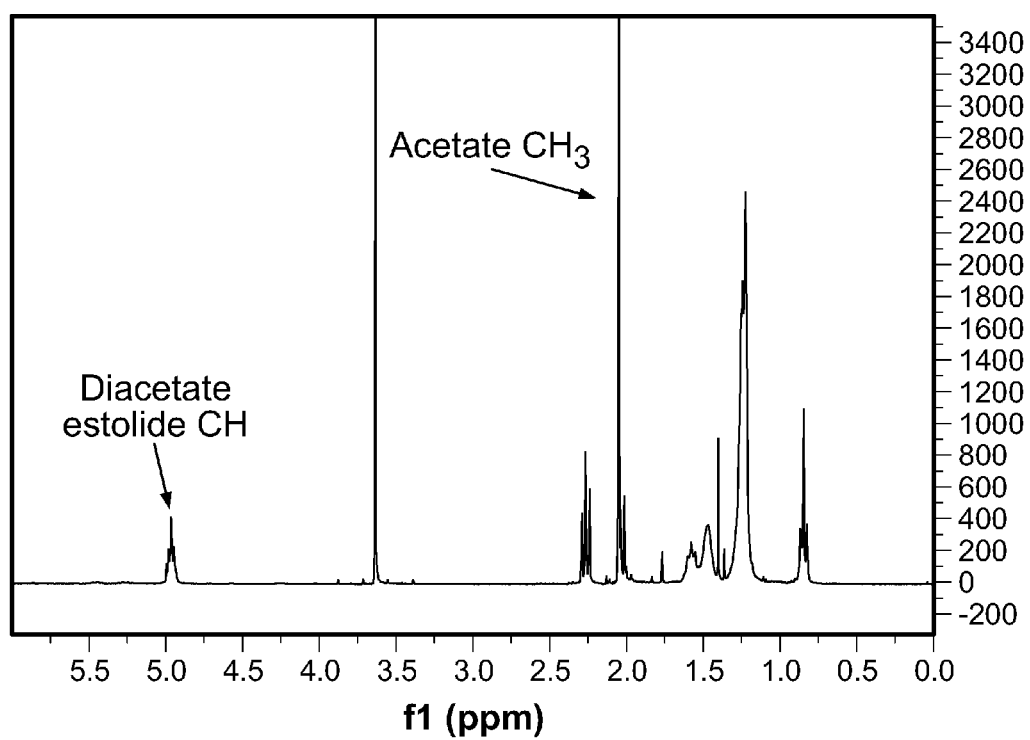
FIG. 17 is a $^1$H NMR of acyclic diacetates derived from oleic acid prepared according to Reaction Scheme VI.
Figure 18:
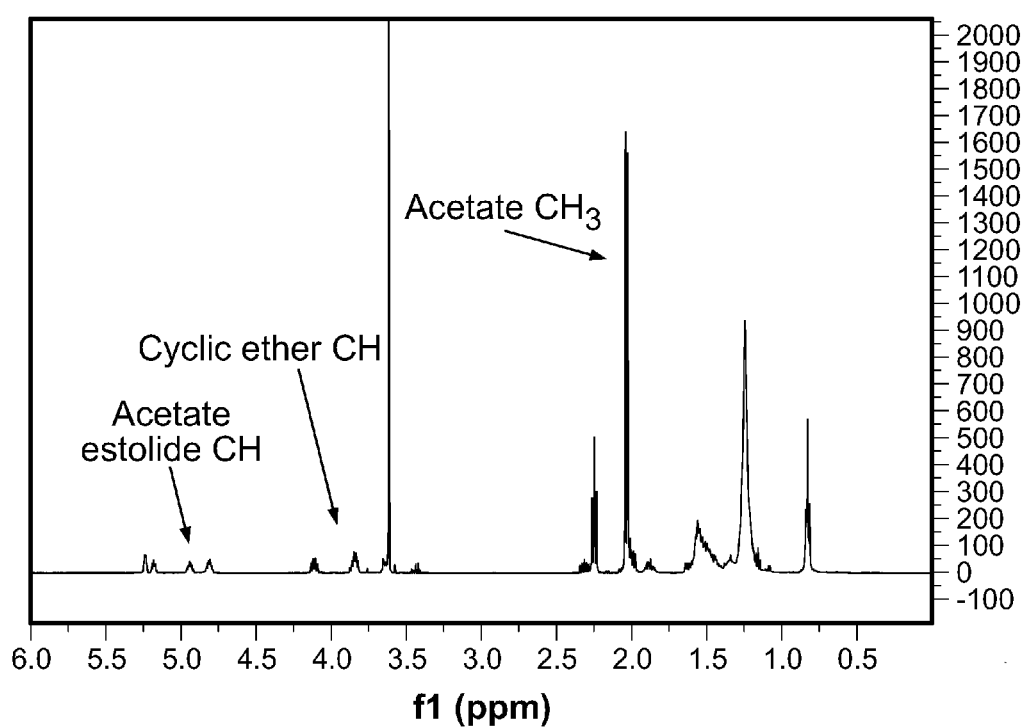
FIG. 18 is a $^1$H NMR of cyclic branched acetates prepared according to Reaction Scheme VI.
Figure 19:
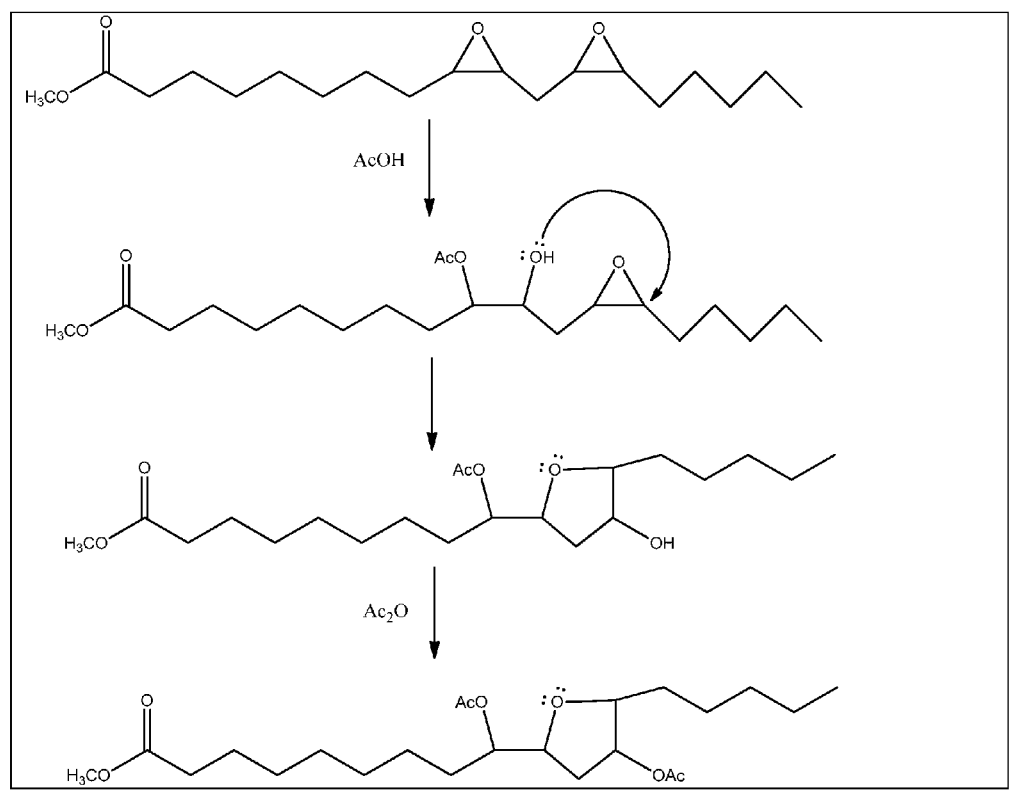
FIG. 19 is an illustration of the mechanism of cyclic ether formation during acetylation according to Reaction Scheme VI.

Based on the information gathered from the separation of the components it can be deduced that each of the different fatty acid esters reacts differently over the course of the epoxidation and acetylation reactions. The saturated fatty acid esters, comprising ~15% of the composition, do not participate in the epoxidation reactions due to the absence of double bonds available for epoxidation and thus no ring opening and acetylation can occur. The oleic fatty acid methyl esters epoxidize then ring open to form diacetates at the site of unsaturation and account for ~20% of the composition of the final product. This material (acyclic diacetates) is shown in FIG. 16 and the corresponding $^1$H NMR is shown in FIG. 17. The majority of the epoxidized fatty acid methyl esters derived from linoleic acid undergo ring opening during the acetylation that cyclizes the fatty acid to form a 5 or 6 membered ether rings like those shown in FIG. 16 by the mechanism shown in FIG. 19. These cyclic branched structures compose ~30-40% of the final product. The $^1$H NMR of these materials is shown in FIG. 18. The remainder of the material, ~20%, contains oligomeric esters of the previous materials.

Figure 20:
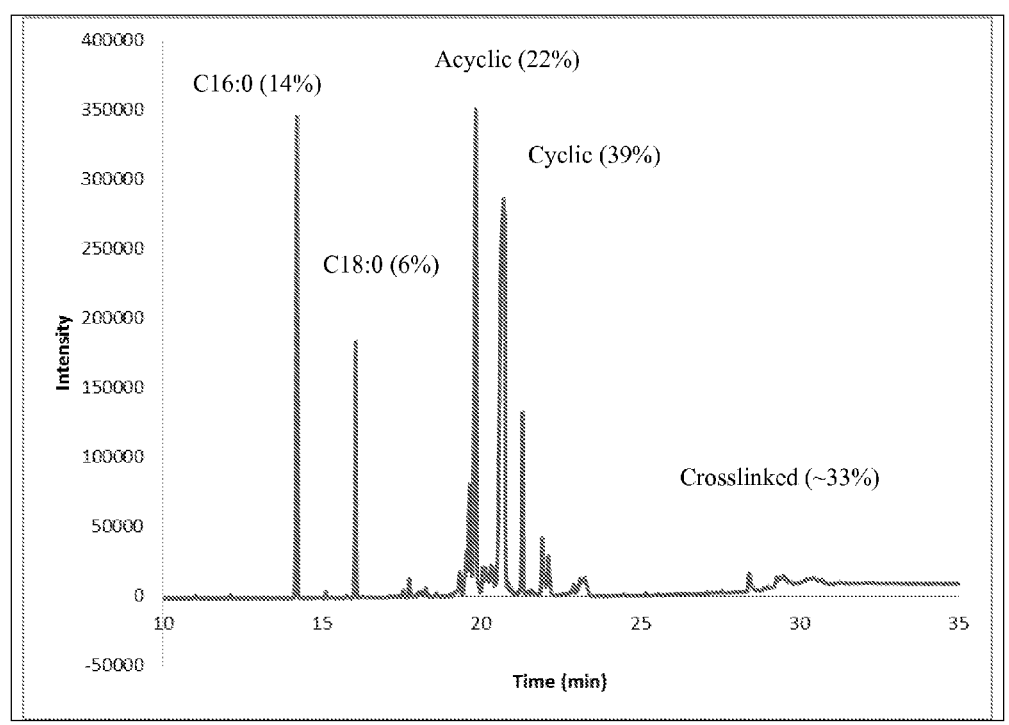
FIG. 20 is a GC chromatogram of the AFAME mixture prepared according to Reaction Scheme VI.

FIG. 20 is a gas chromatogram of the AFAME mixture.

A number of embodiments of the invention have been described. Nevertheless, it will be understood that various modifications may be made without departing from the spirit and scope of the invention. Accordingly, other embodiments are within the scope of the following claims.

What is claimed is:

1. A composition comprising estolide esters of vegetable oil fatty acid alkyl esters, where the vegetable oil has an unsaturation of greater than 90 IV, the fatty acid alkyl esters comprise unsaturated and saturated fatty acid alkyl esters, and each unsaturated fatty acid alkyl ester has greater than one estolide ester functionality on average.

2. A composition according to claim 1 wherein the vegetable oil is selected from the group consisting of soybean oil, canola oil, rapeseed oil, sunflower oil, corn oil, safflower oil, camelina oil, linseed oil, and combinations thereof.

3. A composition according to claim 1 wherein the vegetable oil comprises soybean oil.

4. A composition according to claim 1 wherein the vegetable oil comprises canola oil.

5. A composition according to claim 1 wherein the vegetable oil fatty acid alkyl esters comprise $C_1$-$C_4$ alkyl esters.

6. A composition according to claim 5 wherein the vegetable oil fatty acid alkyl esters comprise a methyl ester.

7. A composition according to claim 5 wherein the vegetable oil fatty acid alkyl esters comprise an isobutyl ester.

8. A composition according to claim 5 wherein the vegetable oil fatty acid alkyl esters comprise methyl and isobutyl esters.

9. A composition according to claim 1 wherein the vegetable oil fatty acid alkyl esters are fully estolided.

10. A composition according to claim 1 wherein the estolide esters are derived from carboxylic acids having 1 to 4 carbon atoms.

11. A composition according to claim 10 wherein the estolide esters are acetate esters.

12. A composition comprising a polymer matrix and the composition of claim 1 in an amount sufficient to plasticize the polymer matrix.

13. A composition according to claim 12 wherein the polymer matrix comprises polyvinyl chloride.

14. A composition according to claim 12 wherein the polymer matrix comprises a biopolymer.

15. A composition according to claim 14 wherein the biopolymer comprises a polylactide polymer.

16. A composition according to claim 14 wherein the biopolymer comprises a cellulosic polymer.

17. A method of making a composition comprising:
 (a) treating vegetable oil fatty acid alkyl esters comprising unsaturated and saturated fatty acid alkyl esters, where the vegetable oil has greater than 90 IV, with an oxidizing agent to form a reaction product comprising epoxy and hydroxyl groups covalently bonded to the fatty acid alkyl esters at the site of unsaturation; and
 (b) treating the reaction product with an acylating agent to react the epoxy and hydroxyl groups to form estolide esters covalently bonded to the unsaturated fatty acid alkyl esters such that each fatty acid alkyl ester has greater than one estolide ester functionality on average.

18. A method according to claim 17 comprising:
 (a) treating the vegetable oil fatty acid alkyl esters with a lower carboxylic acid and an oxidizing agent comprising hydrogen peroxide to form the reaction product comprising epoxy and hydroxyl groups covalently bonded to the fatty acid alkyl esters at the site of unsaturation; and
 (b) treating the reaction product with the acylating agent to form the estolide esters.

19. A method according to claim 17 comprising:
 (a) treating the vegetable oil fatty acid alkyl esters with a peroxy lower carboxylic acid to form a first reaction product comprising epoxy groups covalently bonded to the fatty acid alkyl esters at the site of unsaturation;
 (b) treating the first reaction product with a lower carboxylic acid to form a second reaction product comprising acetoxy and hydroxyl groups covalently bonded to the unsaturated fatty acid alkyl esters at the site of unsaturation; and
 (c) treating the second reaction product with the acylating agent to form the estolide esters.

20. A method according to claim 19 comprising treating the first reaction product with the lower carboxylic acid together with the acylating agent to form the estolide esters.

* * * * *